(12) United States Patent
Lewellen et al.

(10) Patent No.: US 7,312,461 B2
(45) Date of Patent: Dec. 25, 2007

(54) LAPAROSCOPIC TUMOR THERAPY USING HIGH ENERGY ELECTRON IRRADIATION

(75) Inventors: John W. Lewellen, Plainfield, IL (US); John Noonan, Naperville, IL (US)

(73) Assignee: UChicago Argonne LLC, Chicago, IL (US)

( * ) Notice: Subject to any disclaimer, the term of this patent is extended or adjusted under 35 U.S.C. 154(b) by 314 days.

(21) Appl. No.: 11/143,837

(22) Filed: Jun. 2, 2005

(65) Prior Publication Data

US 2006/0060793 A1 Mar. 23, 2006

Related U.S. Application Data

(60) Provisional application No. 60/611,612, filed on Sep. 21, 2004.

(51) Int. Cl.
*H01J 1/50* (2006.01)

(52) U.S. Cl. ............... 250/396 ML; 250/492.3; 250/492.1; 250/455.11; 250/505.1; 250/206.1; 250/206.2; 250/208.2; 378/197; 378/17; 378/65; 378/119; 378/145; 378/64; 378/137; 378/138; 378/121; 315/5.41; 315/5.42; 356/400; 356/138; 600/1; 600/3; 600/427; 600/9; 607/101; 424/1.49; 424/1.57; 424/1.69; 424/9.34; 424/1.85

(58) Field of Classification Search ............ 250/492.1, 250/206.1, 206.2, 492.3, 455.11, 453.11, 250/396 ML, 208.2, 505.1; 356/138, 400; 378/205, 197, 17, 65, 119, 145, 64, 137, 138, 378/121; 315/5.41, 5.42; 600/1, 3, 427, 600/9; 607/101; 424/1.49, 1.57, 1.69, 9.34, 424/1.85

See application file for complete search history.

(56) References Cited

U.S. PATENT DOCUMENTS

| | | | |
|---|---|---|---|
| 4,800,100 A | 1/1989 | Herbots et al. | |
| 4,888,766 A | 12/1989 | Dolezal et al. | |
| 4,963,823 A | 10/1990 | Otto et al. | |
| 5,161,546 A | 11/1992 | Bronn | |
| 5,190,516 A | 3/1993 | Bronn | |
| 5,321,271 A * | 6/1994 | Schonberg et al. | 250/492.3 |
| 5,452,720 A | 9/1995 | Smith et al. | |
| 5,528,652 A | 6/1996 | Smith et al. | |
| 5,534,677 A * | 7/1996 | Elmer et al. | 219/121.35 |
| 5,737,384 A | 4/1998 | Fenn | |
| 5,783,914 A | 7/1998 | Hiramoto et al. | |
| 5,944,749 A | 8/1999 | Fenn | |
| 6,078,036 A * | 6/2000 | Cook et al. | 250/206.1 |
| 6,683,318 B1 | 1/2004 | Haberer et al. | |
| 7,167,540 B2 * | 1/2007 | Muller et al. | 378/65 |
| 7,183,563 B2 * | 2/2007 | Avnery | 250/492.3 |
| 2004/0002202 A1 | 1/2004 | Horsky et al. | |
| 2004/0113099 A1 * | 6/2004 | Eickhoff et al. | 250/492.3 |
| 2005/0226378 A1 * | 10/2005 | Cocks et al. | 378/65 |

OTHER PUBLICATIONS

Intrabeam System, For Intraoperative Radiotherapy Therapy, Radiotherapy Solutions from Carl Zeiss.

* cited by examiner

*Primary Examiner*—Jack Berman
*Assistant Examiner*—Meenakshi S Sahu
(74) *Attorney, Agent, or Firm*—Joan Pennington

(57) ABSTRACT

A laparoscopic tumor therapy method and an articulated electron beam transport system are provided for use with a high power, long focus electron source for tumor therapy. The high power, long focus electron source generates an e-beam. The e-beam is transported through a laparoscopic tube proximate a target tumor for electron irradiation therapy.

13 Claims, 18 Drawing Sheets

100

100

F = 1300 MHz

F = 2700 MHz

FUNDAMENTAL CAVITY FIELD FOR EXEMPLARY TEST GEOMETRY

1000

OVERVIEW OF
PLANAR FOCUSING CATHODE
IN RF CAVITY

ELECTRIC FIELD
CONTOURS

1400

1500

Radius of curvature [m] vs Distance [m]

Final coordinate [mm] vs Distance [m]

LAPAROSCOPIC TUMOR THERAPY USING HIGH ENERGY ELECTRON IRRADIATION

This application claims the benefit of U.S. Provisional Application No. 60/611,612, filed on Sep. 21, 2004.

CONTRACTUAL ORIGIN OF THE INVENTION

The United States Government has rights in this invention pursuant to Contract No. W-31-109-ENG-38 between the United States Government and Argonne National Laboratory.

FIELD OF THE INVENTION

The present invention relates to novel applications of the invention disclosed in U.S. Ser. No. 10/887,142 filed Jul. 8, 2004, entitled FIELD EMISSION CATHODE GATING FOR RF ELECTRON GUNS AND PLANAR FOCUSING CATHODES which embodied a method for implementing a unique electron gun, thus allowing high quality electron beams with high repetition rates to be produced. More particularly, the present invention relates to a laparoscopic tumor therapy method and an articulated electron beam transport system used with a high power, long focus electron source for tumor therapy.

DESCRIPTION OF THE RELATED ART

One form of cancer treatment is irradiation with high-energy particles, such as x-rays, protons, and neutrons. The tumor cells are destroyed by radiation damage. However, the particle irradiation also damages normal body cells and organs that are between the accelerator and the tumor.

One of the primary difficulties in performing cancer therapy with electrons is the small penetration depth; that is, the shallow penetration of even moderate-energy electrons to high-energy electrons into human tissue generally has restricted the application of electron beam cancer therapy to skin and immediate subdermal applications.

Most radio frequency (RF) electron guns constructed to date use either thermionic cathodes or photocathodes as their electron sources. Thermionic cathodes, which use high temperatures to induce electron emission from the cathode material, constantly emit electrons whenever the electric field in the gun is in the correct phase to accelerate electrons away from the cathode. Photocathodes use a light source, typically a high-power laser, to extract electrons from the photocathode surface.

Thermionic-cathode RF electron guns can typically produce very high average power electron beams, because of the continuous nature of the electron emission from the cathode, but can suffer from degraded beam quality because the electron emission cannot be gated to a particular fraction of an RF period. In addition, due to the requirements for high temperatures (ca 1300 C), thermionic cathodes are generally unsuited for use in superconducting RF electron guns (which generally require operating temperatures around four degrees above absolute zero).

Photocathode RF electron guns can produce very high-quality (bright) electron beams, because the use of a laser allows electron emission to be gated to a specific portion of the RF period, but most drive lasers cannot produce a laser pulse at every RF period. Therefore, the average beam power is typically lower than for a comparable thermionic-cathode RF electron gun. Photocathodes in common use typically offer a choice between either long lifetime and poor efficiency thus requiring a far larger drive laser, or poor lifetime and high efficiency requiring the use of a large cathode fabrication and processing system adjacent to the electron gun.

Field emission cathodes have generally not found widespread use in RF electron guns because they will, all other things being equal, emit the most charge when the applied electric field is highest. This is generally not the most desirable time for electron emission, and would result in a very poor-quality beam.

A concave cathode surface can be used for focusing an electron beam for RF electron guns. This approach, however, has two primary disadvantages. First, the focusing thus provided is fixed; for any reasonable cathode design, altering the radius of curvature in situ while maintaining the surface quality required to support high RF field strengths does not appear to be practical. Second, because the cathode is curved, unless a specially prepared drive laser is used, electron emission will start at the edges of the cathode before the center, and will likewise end at the edges of the cathode before ending at the center. These two effects are the primary reason such techniques are not more widely used in existing electron gun designs. In particular, the inability to alter the radius of curvature of the cathode, in effect the focusing force has been seen as a strong disadvantage.

Principal objects of the present invention are to provide a laparoscopic tumor therapy method and an articulated electron beam transport system used with a high power, long focus electron source for tumor therapy.

Other important objects of the present invention are to provide such laparoscopic tumor therapy method and articulated electron beam transport system substantially without negative effect and that overcome some disadvantages of prior art arrangements.

SUMMARY OF THE INVENTION

In brief, a laparoscopic tumor therapy method and an articulated electron beam transport system are provided for use with a high power, long focus electron source for tumor therapy. The high power, long focus electron source generates an e-beam. The e-beam is transported through a laparoscopic tube proximate a target tumor for electron irradiation therapy.

In accordance with features of the invention, to perform the tumor therapy, a small incision is made proximate a target tumor inside a patient's body and the laparoscopic tube then is inserted and positioned to the edge of the tumor. The long-focus electron source is positioned to align with the laparoscopic transport tube. The tumor is then electron irradiated. The laparoscopic tube is a hard-walled laparoscopic tube that transports the electron beam to the tumor without irradiating other body parts.

In accordance with features of the invention, the articulated electron beam transport system used with the high power, long focus electron source for tumor therapy allows the transport of an electron beam to a target cancer site with minimally invasive surgery. The beam is steered to irradiate tumors that are not in straight, line-of-sight view from the electron beam source. The articulated electron beam transport system includes a focusing/defocusing (FODO) lattice with each element articulated; a FODO with cell-by-cell articulation; and a solenoid lens transport.

Electron irradiation of the invention provides advantages over x-rays, neutrons, and protons. Electrons attenuate in very short distances in solids, where other particles, such as x-rays, neutrons, and protons have long attenuation paths.

As a result by tuning the RF electron gun energy, the e-beam substantially is absorbed in the tumor alone.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

In accordance with features of the invention, laparoscopic tumor therapy methods are implemented using a novel high power, long focus electron source. The electron source includes a radio frequency (RF) electron gun with a field-emitter cathode providing a focused electron beam and implements a general method for altering the emission time of a field-emitter cathode with respect to the RF period in the gun. This approach combines the advantages of the thermionic-cathode RF electron gun (beam produced every RF period, no laser needed) with those of a photoinjector (gated emission at the most desirable time, high brightness, superconducting RF-compatible). The resulting high power, long focus electron source enables broad applicability across a number of fields.

In accordance with features of the novel high power, long focus electron source, a planar focusing cathode, also referred to as a standoff cathode, provides a means of focusing an electron beam emitted from the cathode of a high-brightness RF electron gun, without requiring the use of either magnetic fields, or a curved cathode surface.

In accordance with features of the invention, methods and laparoscopic tumor therapy apparatus for implementing laparoscopic tumor therapy methods are illustrated and described with respect to FIG. 14-22. In FIGS. 1-13, the novel high power, long focus electron source used for implementing beam processing methods is illustrated and described and is disclosed in U.S. patent application Ser. No. 10/887,142 by the present inventors filed Jul. 8, 2004, entitled FIELD EMISSION CATHODE GATING FOR RF ELECTRON GUNS AND PLANAR FOCUSING CATHODES, and assigned to the present assignee. The subject matter of the above-identified patent application is incorporated herein by reference.

Figure 1:
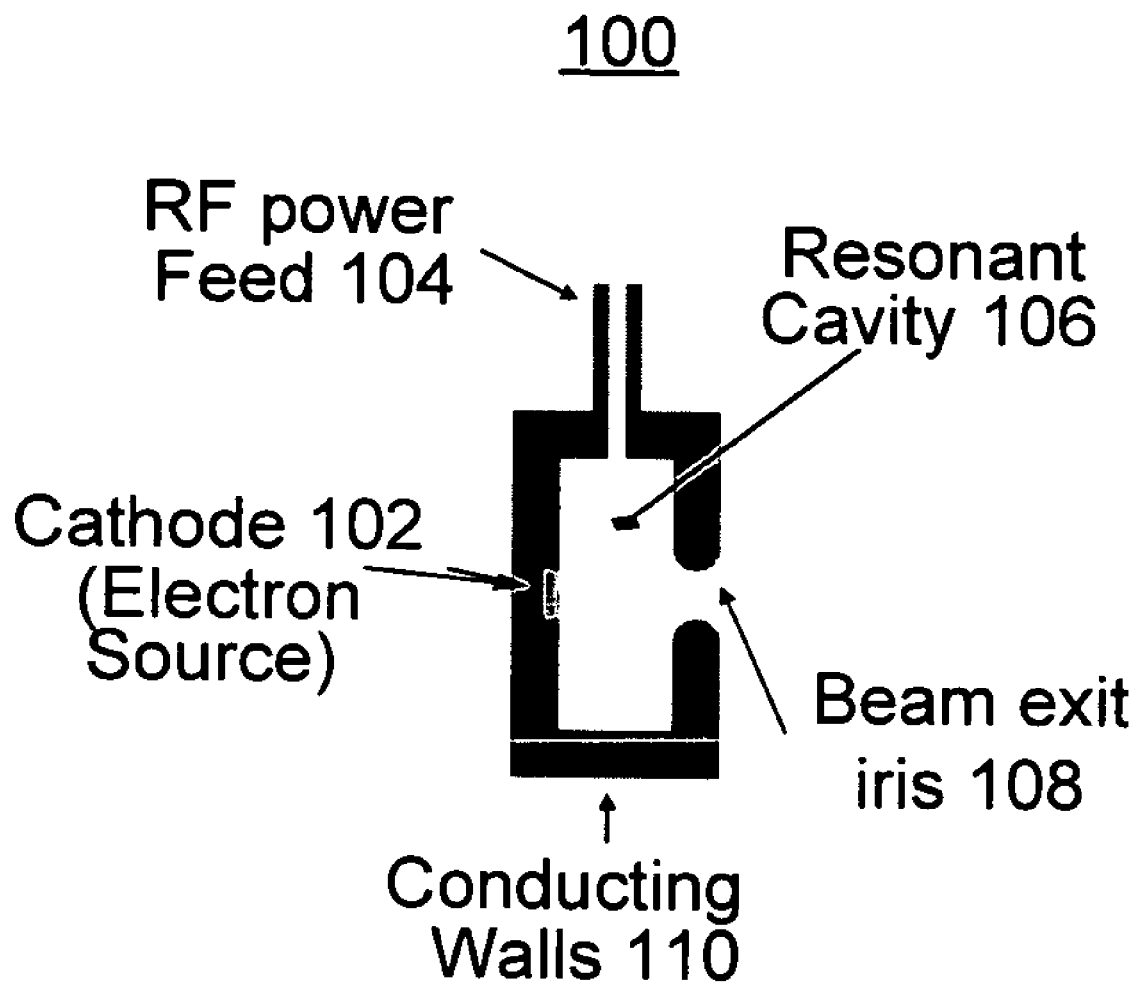
FIG. 1 is a schematic diagram illustrating an exemplary 1-cell RF electron gun for implementing methods in accordance with the present invention.

Having reference now to the drawings, in FIG. 1 there is shown an exemplary RF electron gun generally designated by the reference character 100 that can be used for implementing methods in accordance with the present invention. The RF electron gun 100 is a single cell or 1-cell RF electron gun that is essentially a box in which an oscillating electromagnetic field is generated. The RF electron gun 100 includes a cathode 102 that provides an electron source. The RF electron gun 100 includes an RF power feed 104 that is used to establish an oscillating electromagnetic field inside a resonant cavity 106. This field is used to accelerate electrons emitted from the cathode 102 out a beam exit iris 108 provided within conducting walls 110 defining the resonant cavity 106.

In general, RF electron guns work by establishing an oscillating electromagnetic field inside a cavity, or series of cavities, such as resonant cavity 106 defined by conducting walls 110. This field is used to accelerate electrons emitted from a cathode, down the bore of the gun, and out an exit port, such as from cathode 102 and out beam exit iris 108. The phase of the RF field at which a given electron is emitted from the cathode 102 determines whether it can exit the cavity 106, and, if so, at what energy. Electrons attempting to leave the cathode 102 too early in phase, before the so-called zero-crossing, cannot exit the cathode at all because the electric field in the cavity is the wrong sign. Electrons emitted too late in phase cannot exit the RF electron gun 100 before the electric field reverses sign; these electrons will be decelerated before they can exit the gun. This can cause the overall electron beam quality to suffer. Electrons emitted still later will have their direction of flight reversed, and will return to strike somewhere in the vicinity of the cathode. This phenomenon is called back-bombardment.

Figure 2:
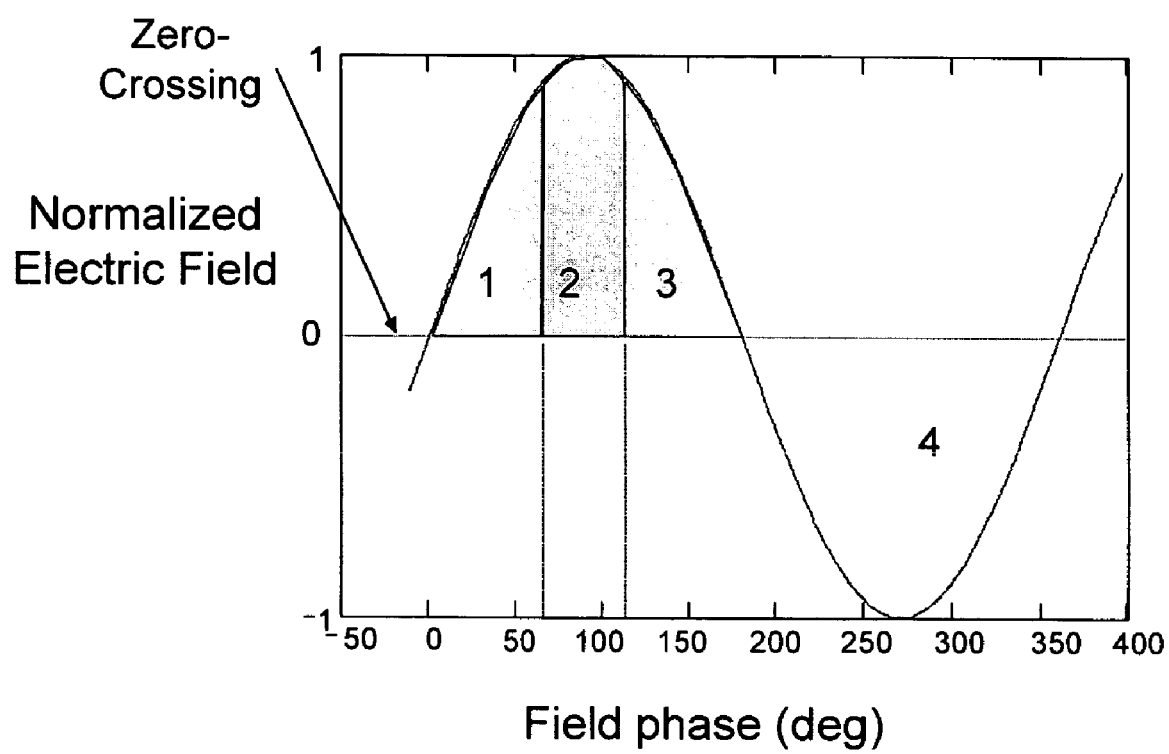
FIG. 2 is a chart illustrating beam emission timing for the RF electron gun of FIG. 1.

FIG. 2 illustrates, for a single RF period, the fate of emitted electrons as a function of phase including a plurality of regions respectively labeled 1, 2, 3 and 4. Although the exact dependence of electron beam quality and energy as a function of launch phase depends very strongly on details of the gun design and construction, some general features can be identified. Electrons emitted during region 1, between 0 degrees and (approximately) 60 degrees, will exit the gun with reasonable beam quality and comparatively high electron beam energy. Electrons emitted during region 2 will exit the gun, but with greatly degraded beam quality and lower beam energy. Generally, there is a smooth transition between regions 2, and 3, from which electrons will be emitted from the cathode but which will not be able to exit the gun; many of these electrons, in fact, will reverse direction and strike the cathode. Finally, in region 4, electrons cannot be emitted from the cathode because the electric field on the cathode is the wrong sign. Other properties of the beam, such as divergence, will change smoothly with emission phase.

Having reference to FIG. 2, this provides a ready illustration of the relative advantages and disadvantages of photocathodes vs. thermionic cathodes. Thermionic cathodes emit electrons continuously, and so can generate very high average power electron beams; however, much of their emission occurs during regions 2 and 3. Electrons emitted during region 3 are by definition not relevant to the final electron beam quality, but they still take energy to accelerate. The entire beam consists of a mixture of electrons emitted during region 1 and region 2, resulting in a considerably lowered overall beam quality.

Photocathodes emit electrons only when struck with an appropriate pulse of light, as from a drive laser. Thus, it is possible to gate the electron emission to only a very narrow slice within region 1, yielding a very high-quality electron beam. The drive laser, however, adds considerable cost and complexity to the system, and cathode material limitations appear, at the present time, to prohibit both high-duty-cycle and highly robust operation.

Finally, field emission (FE) cathodes operate by using strong electric fields to pull electrons from the cathode material directly. Thus, unlike thermionic cathodes, they do not emit continuously. Unlike photocathodes, their triggering mechanism does not rely on an external event such as the arrival of a laser pulse. Rather, FE cathodes do not emit electrons below a threshold electric field. Above that threshold, which can be varied significantly depending on the cathode design, FE cathodes will begin to emit electrons, with the emission current increasing rapidly with increasing electric field.

At first glance, this behavior would seem to make FE cathodes a very appealing alternative to both thermionic and photocathodes. The difficulty, however, lies in that the FE cathode will emit the highest current when the electric field gradient is the strongest; the emission will be symmetric about the 90° point.

Figure 3:
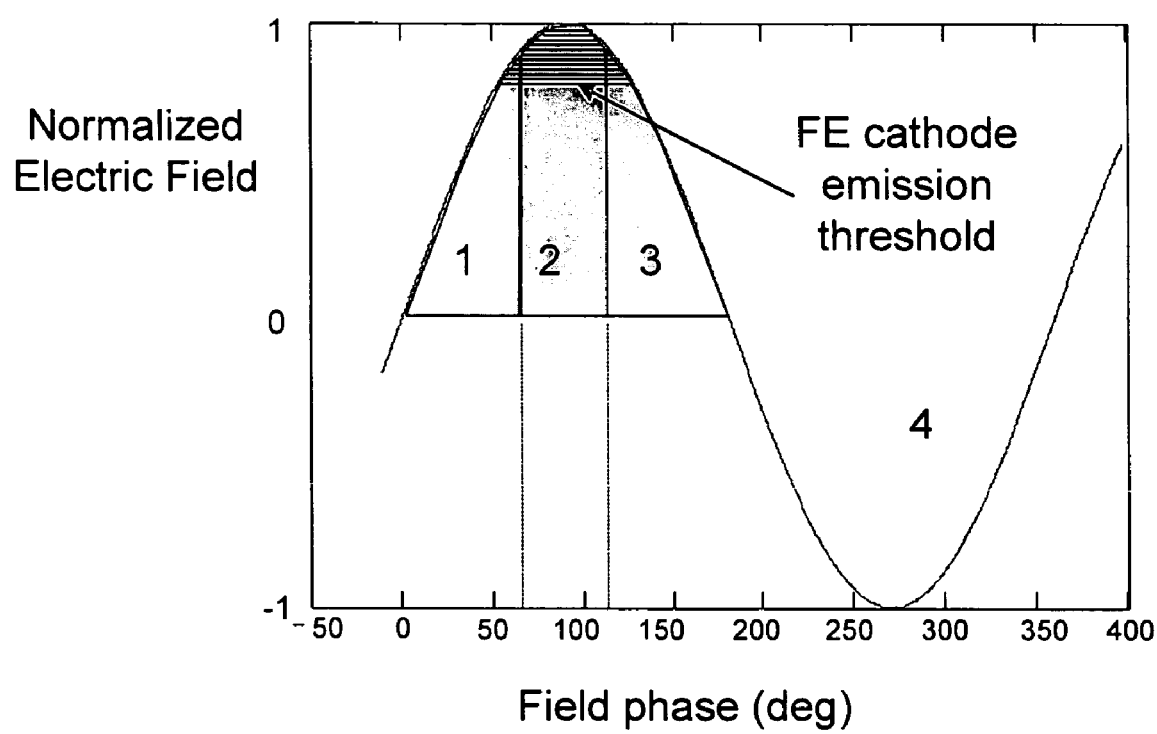
FIG. 3 illustrates the FE cathode emission times during the RF period of FIG. 2 for implementing methods in accordance with the present invention.

FIG. 3 illustrates the FE cathode emission times during the RF period of FIG. 2. It is apparent that the FE cathode will emit most of its beam current during region 2 of the RF period. The resulting beam will typically have a very large energy spread, and very poor transverse quality. Worse, some of the beam, emitted during region 3, may return to the cathode and damage it via the back-bombardment process. In general, the emission from the FE cathode will be too long in duration, and will occur at the wrong part of the RF period.

In fact, this description applies very well to the dark current observed during the operation of some high-field RF photocathode guns, so named as it describes electrons emitted without the presence of a drive laser pulse. In these cases, imperfections on the photocathode surface act as FE cathodes. The resulting beams are typically low energy, with large energy spreads and exceedingly poor transverse beam quality.

Potential mechanisms for addressing some of these shortcomings, such as shortening the cell containing the cathode, do not provide sufficient improvement so as to make the FE cathode a viable choice for RF electron guns.

A given RF cavity is typically capable of supporting many different field patterns oscillating at many different frequencies. A specific pattern at a specific frequency is usually identified as a cavity mode.

Figure 4A:
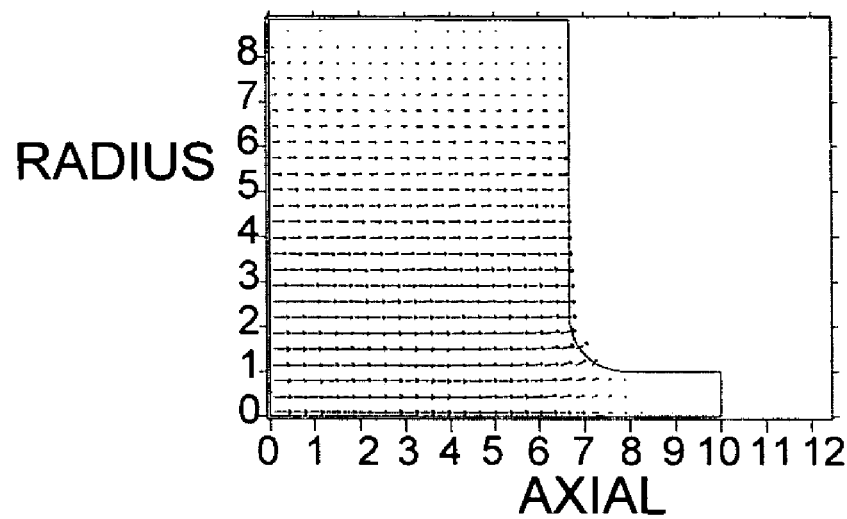
FIGS. 4A and 4B illustrate the two lowest modes or field patterns for the single-cell RF electron gun of FIG. 1 in accordance with the present invention.
Figure 4B:
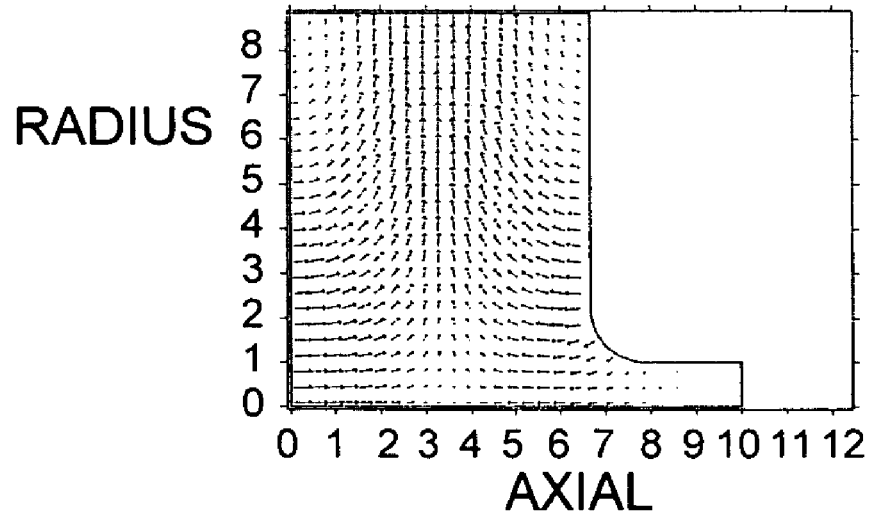

FIGS. 4A and 4B illustrate the two lowest modes, or field patterns, for the same single-cell RF electron gun. Typically, RF electron guns are designed to operate using a single mode in the cavity. Typically, the RF electron gun is designed to use the lowest-frequency, or fundamental, mode. In this case, the two modes shown are the two lowest frequencies the cavity is capable of supporting. The higher frequency of FIG. 4B is not an exact harmonic or integer multiple of the lower frequency of FIG. 4A. Plot axes of FIGS. 4A and 4B are r (radius) vs. z (axial) coordinates. The arrows represent the direction and strength of the electric field in the cavity.

It is possible to tune a cavity such that at least some of the modes are harmonic. For instance, it is possible to tune the cavity such that the third cavity mode oscillates at exactly three times the frequency of the fundamental mode. The fields in the cavity will then beat in phase with each other. (Some work has been performed using such a field sum to generate what appears to be a flat cavity field. The thrust of the prior work, however, had been to generate approximately uniform fields in space rather than in time.)

Figure 5A:
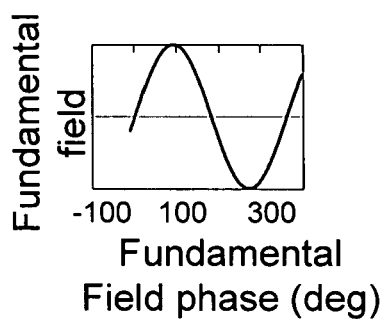
FIGS. 5A, 5B, and 5C illustrate the effect of adding a third-harmonic component to the fundamental, at a particular point in the RF cavity, as a function of the phase of the fundamental field in accordance with the present invention.
Figure 5B:
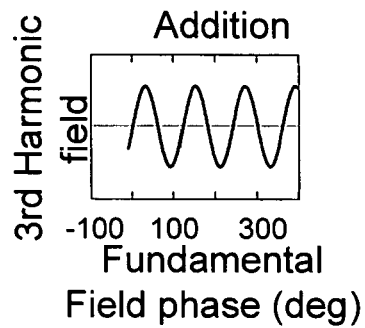
Figure 5C:
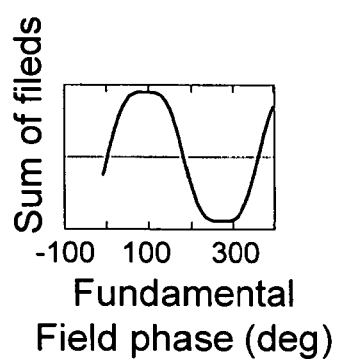

FIGS. 5A, 5B, and 5C illustrate the effect of adding a third-harmonic component to the fundamental, at a particular point in the RF cavity, as a function of the phase of the fundamental field.

Figure 5D:
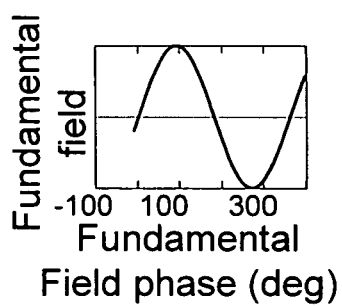
FIGS. 5D, 5E, and 5F illustrate the effect of subtracting a third-harmonic component to the fundamental, at a particular point in the RF cavity, as a function of the phase of the fundamental field in accordance with the present invention.
Figure 5E:
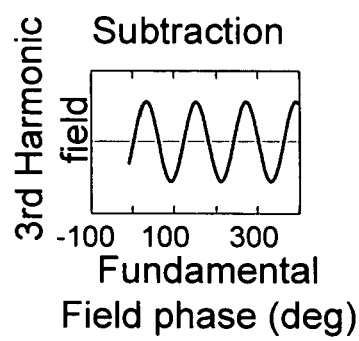
Figure 5F:
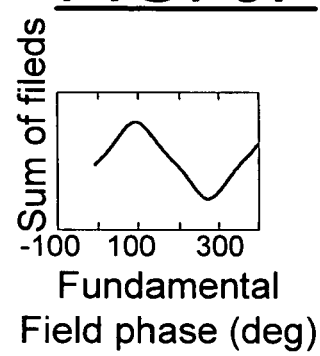

FIGS. 5D, 5E, and 5F illustrate the effect of subtracting a third-harmonic component to the fundamental, at a particular point in the RF cavity, as a function of the phase of the fundamental field.

At first glance, this does not appear to be particularly useful in that, although we can evidently control the duration of the peak field (expand into a flat-top as in FIG. 5C, or sharpen as in FIG. 5F), the peak field is still centered squarely in region 2.

The field addition can be represented as follows:

$$E_{sum}(t) = E_1 \sin(\omega_1 t + \phi_1) + E_3 \sin(3\omega_1 t + \phi_3) \quad (1)$$

where $\omega_1$ represents the angular frequency of the fundamental field, $E_1$, $E_3$ represents the respective amplitude of the fundamental field and the $3^{rd}$-harmonic field, $\phi_1$, $\phi_3$ represents the respective phase of the fundamental field and the $3^{rd}$-harmonic field, and t is time. We can choose to set $\phi_1=0$, and we can also write $E_3=\alpha E_1$ where $\alpha$ is simply a proportionality constant. In FIGS. 5A, 5B, and 5C, in effect, $\alpha=\frac{1}{9}$, and $\phi_3=0°$ for case of addition, and in FIGS. 5D, 5E, and 5F $\alpha=\frac{1}{9}$, and $\phi_3=180°$ for case of subtraction.

Figure 6A:
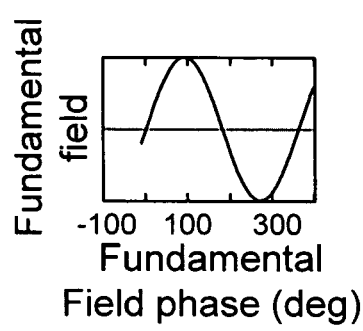
FIGS. 6A, 6B, and 6C illustrate the effect of adding a third-harmonic component to the fundamental, at a particular point in the RF cavity, as a function of the phase of the fundamental field for another selected proportionality constant and phase of the 3rd harmonic field in accordance with the present invention.
Figure 6B:
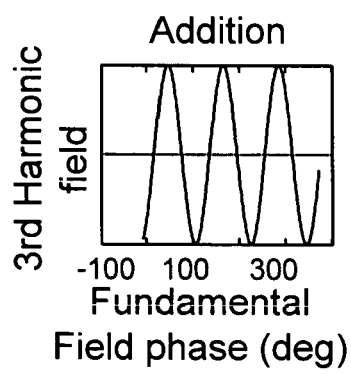
Figure 6C:
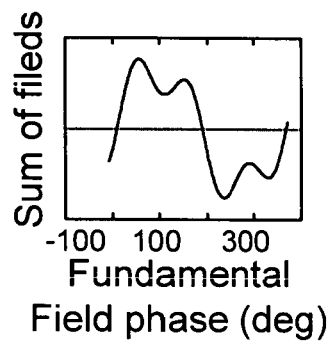

Referring now to FIGS. 6A, 6B, and 6C, $\alpha$ and $\phi_3$ may be set to be whatever values desired. FIGS. 6A, 6B, and 6C illustrate the effect of adding a third-harmonic component to the fundamental, at a particular point in the RF cavity, as a function of the phase of the fundamental field for another selected proportionality constant set to $\alpha=0.4$ and phase of the 3rd harmonic field of $\phi_3=-40°$.

Two features can be seen having reference to FIGS. 6A, 6B, and 6C. First, the width of the peak field has narrowed considerably, compared to the fundamental alone. Second, and most importantly, the peak of the field has shifted from 90° to approximately 50°. Therefore, with an appropriately chosen emission threshold, the FE cathode will emit electrons around the 50° point, within region 1.

Figure 7:
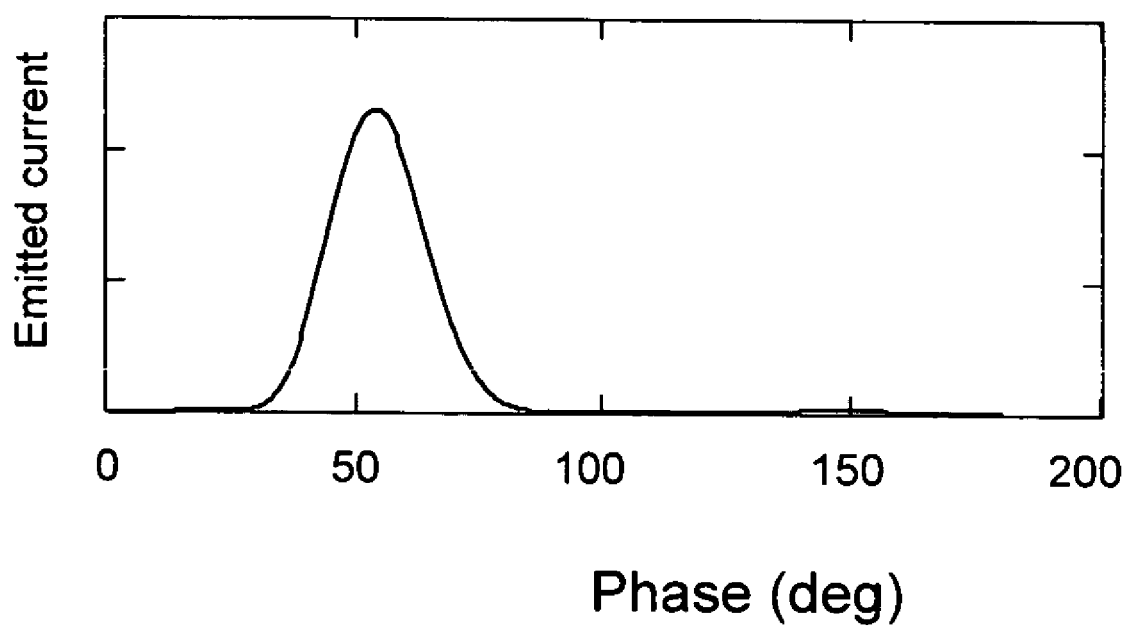
FIG. 7 illustrates an exemplary FE cathode emission profile during the RF period of FIGS. 6A, 6B, and 6C for implementing methods in accordance with the present invention.

FIG. 7 illustrates an example calculated emission profile for the fields shown in FIGS. 6A, 6B, and 6C.

In accordance with features of the invention, by adjusting the phase and strength of the 3rd harmonic field relative to the fundamental field, we cause a field emission cathode to emit electrons at times appropriate for the generation of high-brightness electron beams. The emission time is gated by the combined fields and the response of the FE cathode to the combined fields; much as a photocathode's emission is gated by its drive laser. Like a thermionic cathode, the FE cathode's emission is not determined by the presence or absence of a laser pulse; therefore, the cathode will produce beam at every RF period.

Therefore, this technique of the invention permits the combination of appropriately gated emission, for high-brightness beam production, with emission during every RF period, for high-average-power operation. This summation of fields in the cavity represents, in effect, the first two terms of a Fourier series describing an ideal driving field for a field-emission cathode gun. In principle, additional improvements to the field shape could be made, for example, generating a small flat-top distribution, by adding more fields at higher harmonics. In practice, this rapidly becomes less practical for two important reasons.

First, a reasonable method is required for coupling the harmonic power into the cavity, along with a suitable high-power microwave source. For the style of cavity, such as cavity 106 illustrated in FIG. 1, coupling power into the cavity via an on-axis coupler at the exit of the gun 100 can be provided together with using a cathode stalk or recess region as another input coupler. Adding another harmonic requires another coupling port, for example, machined to even higher precision due to the higher frequency, isolated from the first two harmonics. The same problems must be solved again for each successive harmonic added.

Second, the cavity 106 must be resonant at all harmonic frequencies in order to build up reasonable field strengths. For the lowest cavity mode or the fundamental mode, the cavity radius is the dominant factor in determining resonant frequency. For all other modes, both the cavity radius and the length are important in determining the resonant frequency. Therefore, to an extent, with two harmonics one can set the radius of the cavity to tune for the desired fundamental, and then adjust the length to tune in the 3rd harmonic. This solves the resonant frequency problem without resulting to highly speculative cavity designs.

It should be understood that while it may be possible in principle to add still higher harmonic fields to the cavity, and while this may be of some benefit, the primary concept of gating the field-emission cathode to a useful beam launch time does not depend on doing so. Also by adding the 5th harmonic component, rather than the 3rd harmonic component, does not offer any obvious advantages in terms of beam quality, and results in more peaks in the field sum. The result is that emission is not as cleanly gated to the desired time; instead, emission can occur at multiple times during the fundamental RF period, leading to the risk of contaminating the desired beam.

There are additional considerations to be addressed in order to apply this technique of the invention to produce a viable electron beam source. In particular, in order to obtain the properly gated electron emission as noted above, the 3rd harmonic field has to be quite strong in comparison to the fundamental field. For good beam dynamics in the gun, however, the fundamental field must dominate as the beam moves from the cathode to the exit. The addition of a modest 3rd harmonic field can benefit beam transport, however, the required phase and amplitudes of the 3rd harmonic are shown with respect to FIGS. 5A, 5B, 5C, which is unsuitable for FE cathode gating.

Figure 8:
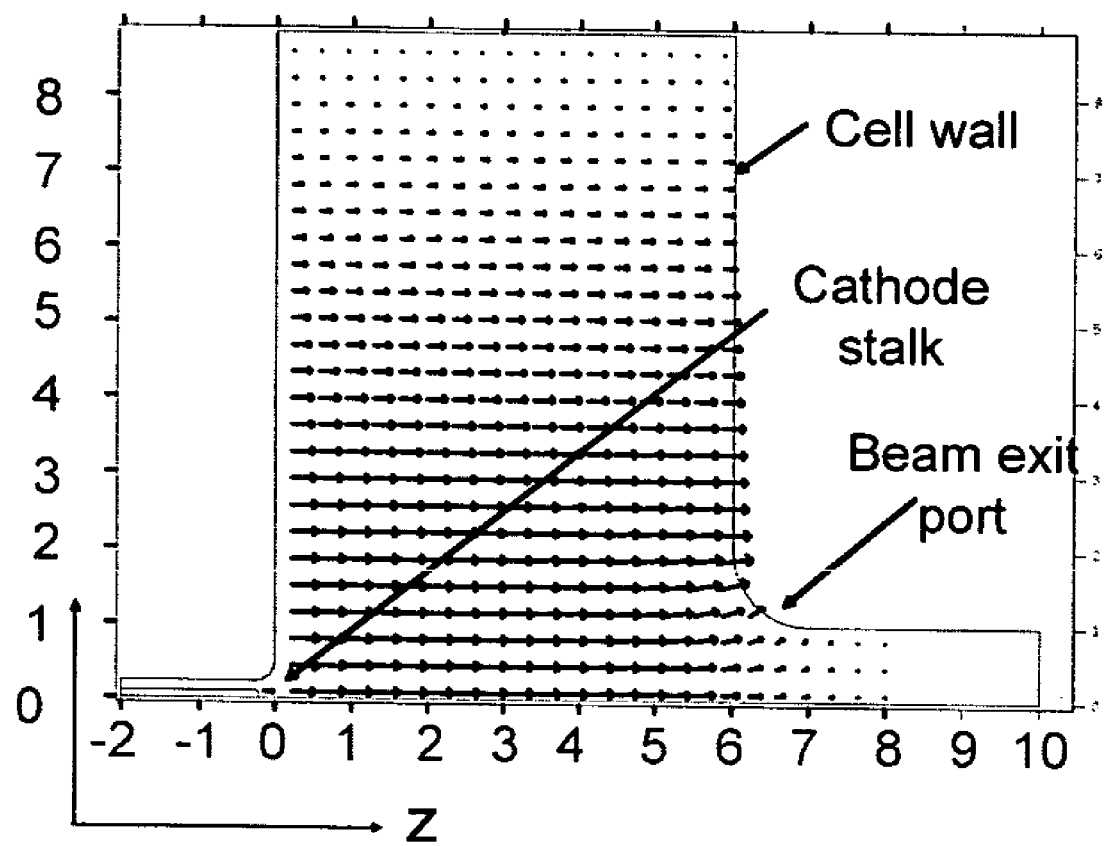
FIG. 8 illustrates FE cathode gun cell test geometry used for simulations in accordance with the present invention.
Figure 11:
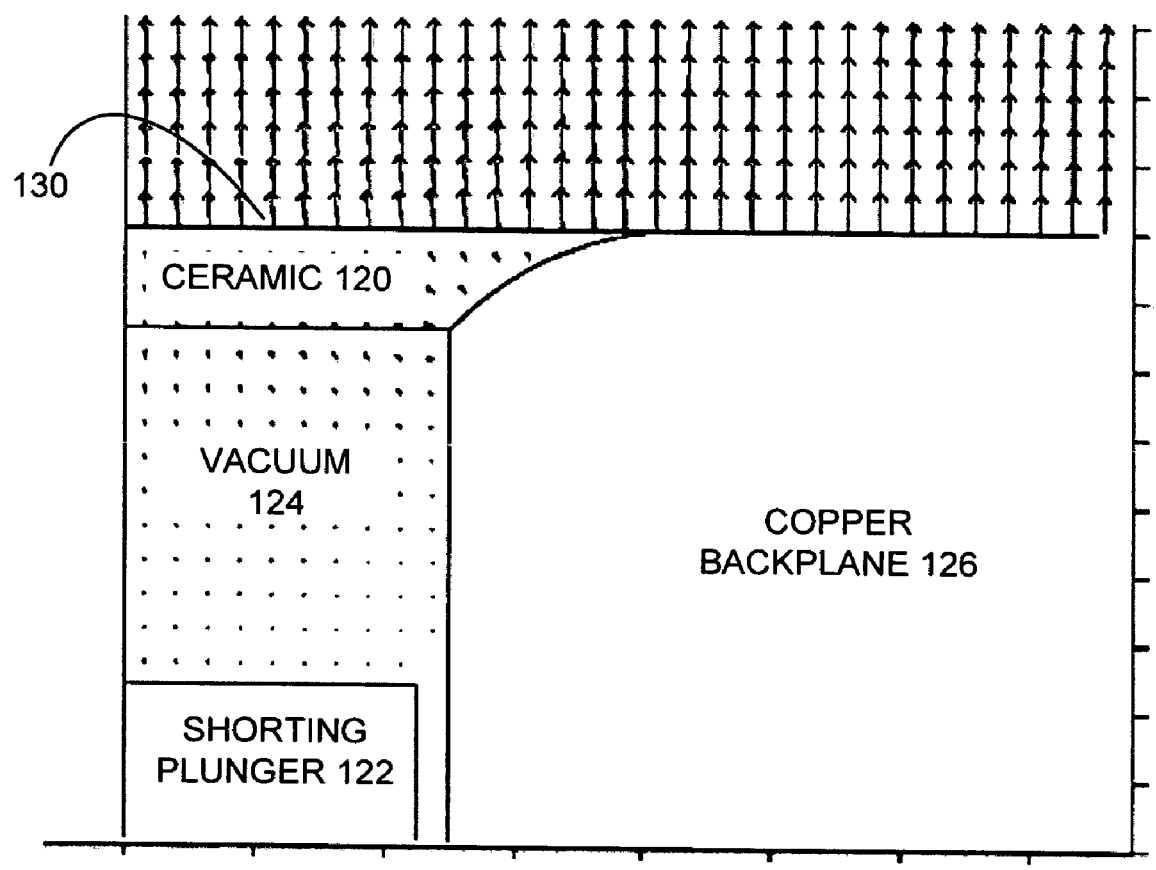
FIG. 11 is a detailed view of the RF electron gun of FIG. 1 illustrating a novel planar focusing cathode that provides a focused electron beam in accordance with the present invention.

A method is therefore required to obtain a strong 3rd harmonic field component at the cathode 102, while minimizing its effects elsewhere in the cavity 106. This is accomplished as follows. The gun cavity 106 contains a recess where the cathode would ordinarily be, for example, as illustrated in FIGS. 8 and 11. The FE cathode is placed on a stalk recessed slightly into this cavity. The 3rd harmonic field will penetrate into the recess more deeply than the fundamental field, due to its higher frequency and, therefore, shorter wavelength.

Thus, the 3rd harmonic field will be strong, relative to the fundamental field, at the cathode surface where it is required to properly gate the FE cathode emission. In the body of the gun, however, the fundamental will dominate, yielding dynamics similar to those of a conventional gun.

FIG. 8 illustrates FE cathode gun cell test geometry used for simulations.

Figure 9:
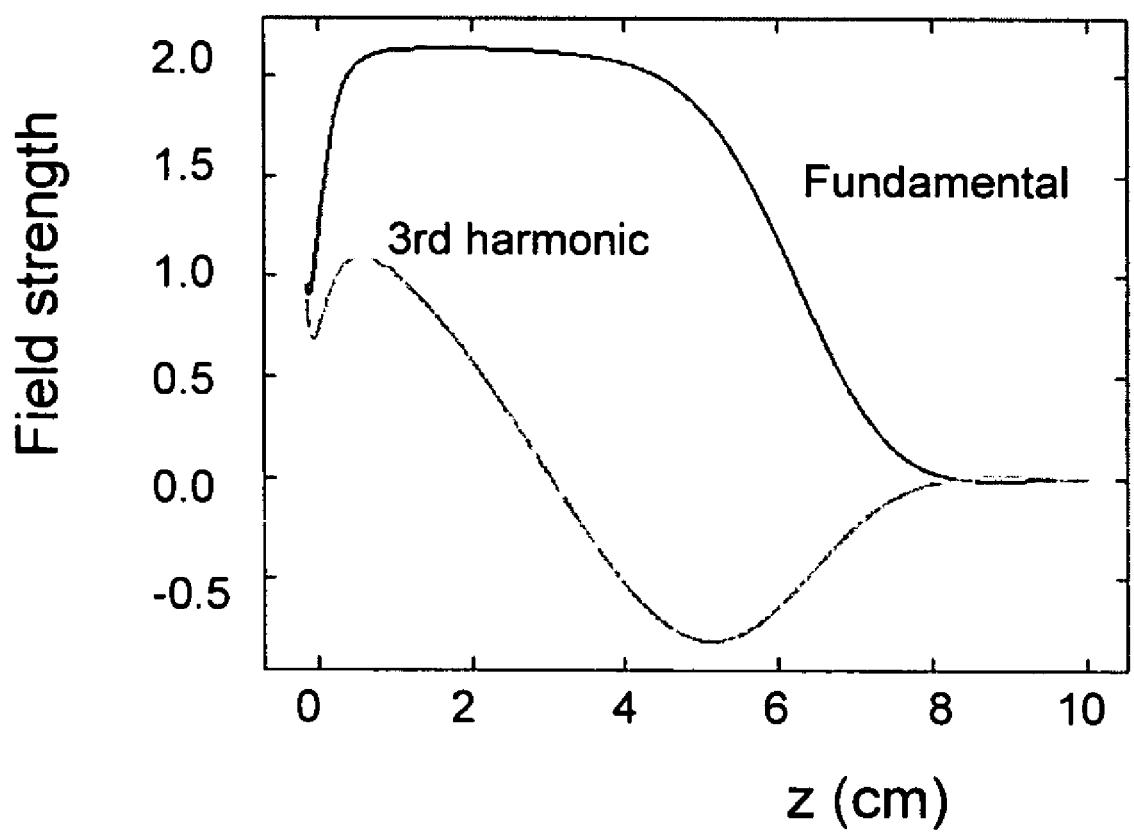
FIG. 9 illustrates the fundamental and 3rd harmonic fields strength plotted as distance along the axis of the gun of FIGS. 1 and 8 in accordance with the present invention.

FIG. 9 illustrates the fundamental and 3rd harmonic fields, plotted as distance along the axis of the gun.

Note that the fundamental field has twice the strength in the body of the cavity as it does at the tip of the cathode and that the 3rd harmonic field is twice as strong at the cathode tip as it is in the majority of the body of the cell. Therefore, for equal fields at the cathode tip, the 3rd harmonic is ¼ as strong in the body of the cell. With $\alpha=0.4$, then, the fundamental is a factor of 10 stronger in the body of the cathode cell. This meets our requirement that the fundamental field dominate the beam dynamics in the main body of the cell.

This is not an ideal process; in particular, the beam energy spread is higher than desired, and further manipulation advantageously is performed to make the beam more generally useful. However, this is true of both photocathode and thermionic-cathode electron guns. The significant advantage here is the ability of the FE cathode gun to produce a beam that can be so manipulated, potentially in a package which is superconducting, and thus makes extremely efficient use of the available RF power. These manipulations are fairly routine.

The examples of FIGS. 8 and 9, and the following sample calculations, are based on the choice of a 1.3 GHz fundamental RF frequency, with a corresponding 3rd harmonic at 3.9 GHz.

Figure 10:
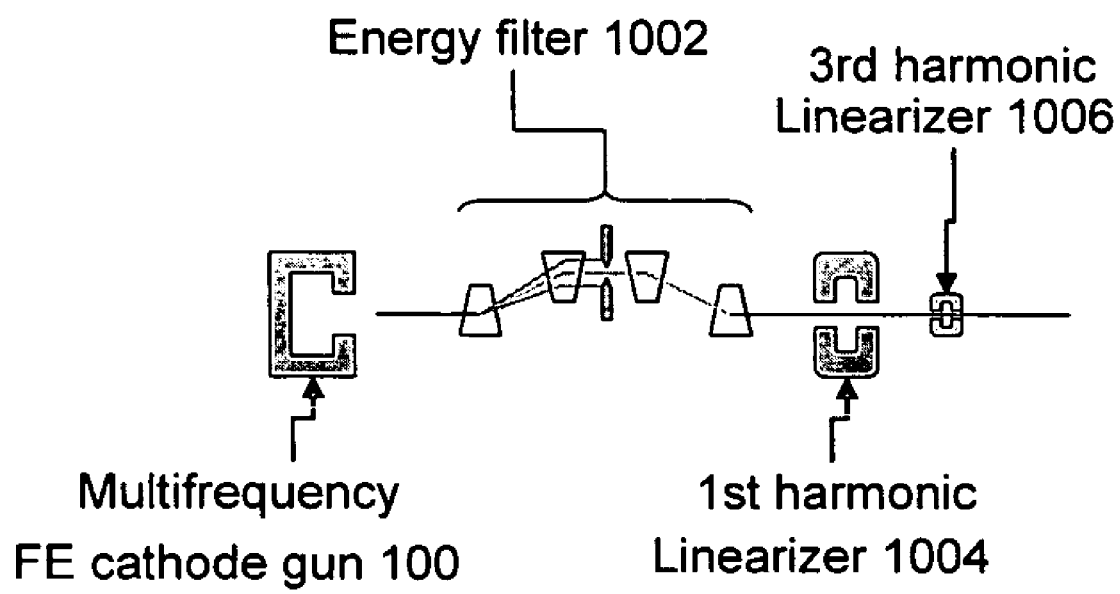
FIG. 10 illustrates an exemplary application of the gun of FIGS. 1 and 8 in accordance with the present invention.

This particular choice of fundamental frequency was driven by three considerations. First, there are several commercial RF power sources available in the range needed for the e-microscope application as illustrated in FIG. 10. Second, L-band cavities are of a size that is a good compromise between machining tolerances, where lower frequencies are better, with compactness. Finally, the TESLA superconducting accelerator structures are designed to operate at L-band, so there is already a large and growing community knowledgeable about making superconducting cavities, and associated systems, in this frequency range. In brief, it should be understood that this particular choice of fundamental frequency simply is a convenient first choice.

It should be understood that the present invention is not limited to this selection of frequency. Considerations exist and arguments can be made for going to either lower or higher frequencies. It should be emphasized and understood that the FE cathode gating method of the present invention will, in general, operate independently of the choice for the fundamental frequency. This is the addition of harmonic fields with a defined relationship in phase; therefore, everything scales with the fundamental frequency. This includes, for instance, the bunch length, which with longer (shorter) frequency will become longer (shorter) in time, but which will have the same length when expressed in terms of degrees of RF phase. This has important implications for beam dynamics also, as it means that the basic performance should be maintainable across a broad range of frequency choices. The ability of the cavity to properly support and accelerate a given beam current does change somewhat with frequency, but in general is more limited by the available RF power than by the particular design of the cavity or choice of resonant frequency.

Figure 12:
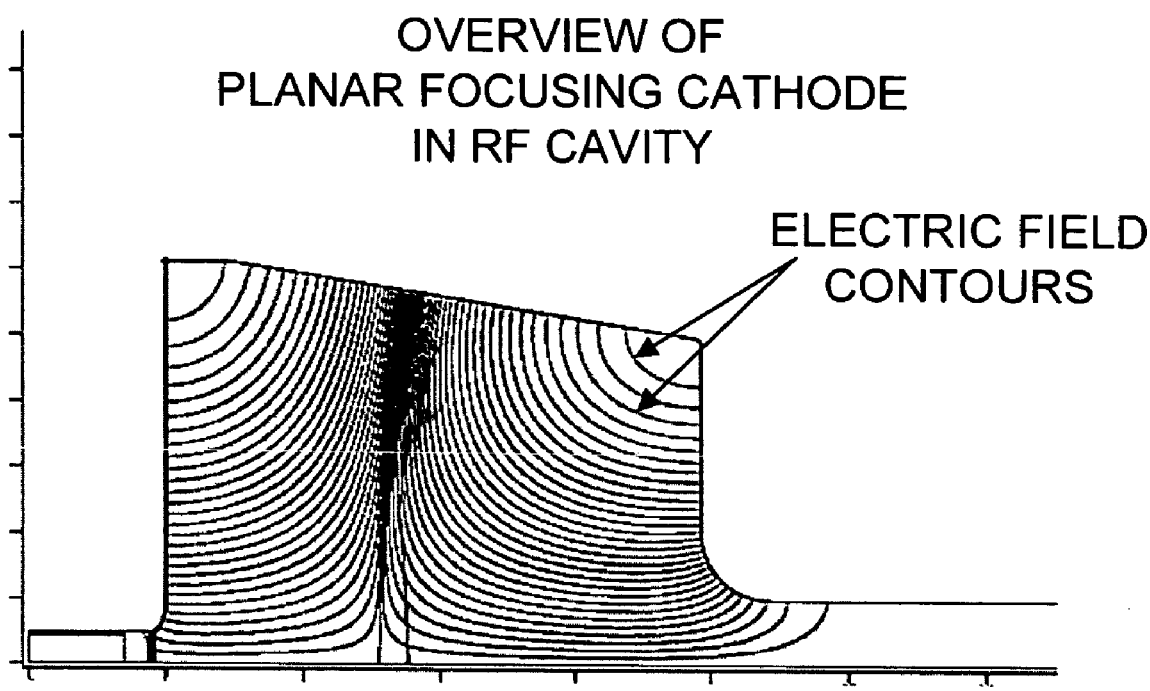
FIG. 12 illustrates exemplary electric field contours of the planar focusing cathode of FIG. 11 in accordance with the present invention.
Figure 13:
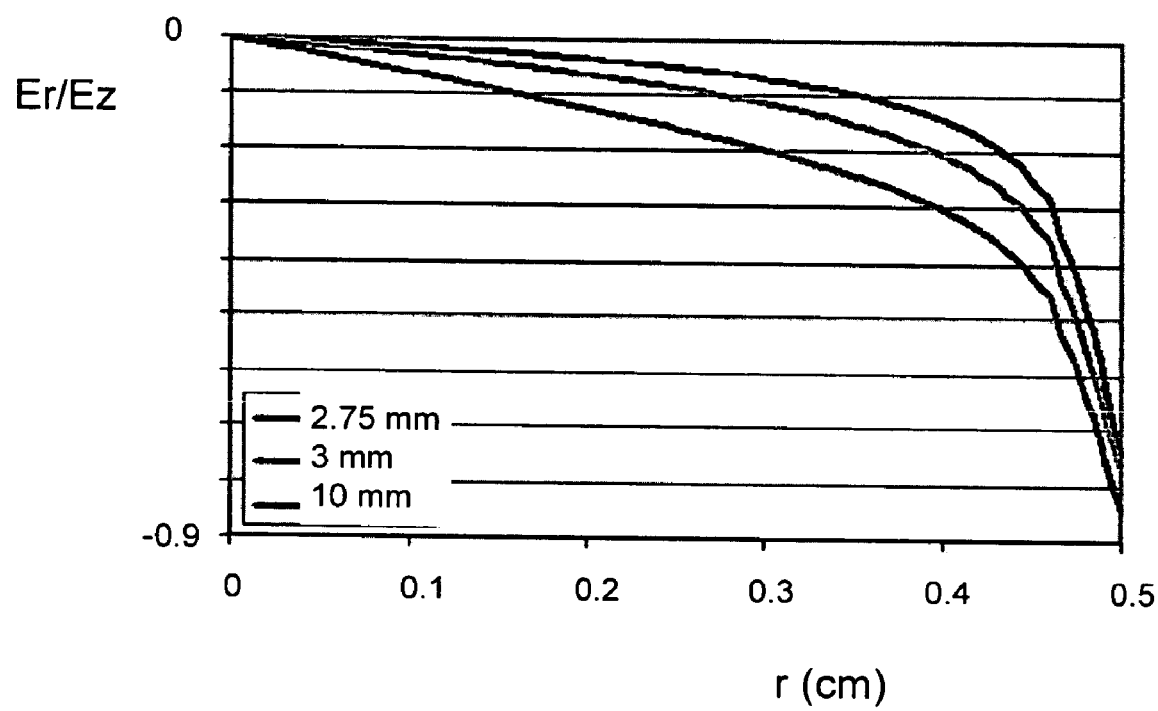
FIG. 13 illustrates exemplary normalized radial electric field at the cathode surface of the planar focusing cathode of FIG. 11 in accordance with the present invention.

These calculations also do not incorporate some of the advanced cathode designs, such as, in particular a planar focusing cathode of the invention as illustrated and described with respect to FIGS. 11, 12, and 13. Such planar focusing cathodes are designed to help counter strong space-charge forces acting on the beam as it leaves the cathode. The sample applications below typically assume very low bunch charges; the modest average beam current comes from every bucket being filled (i.e. one bunch generated per RF period) and the high beam power from the combination of moderate current and high beam energy.

For higher-current applications, such as for a free-electron laser driver, it is anticipated that the planar focusing cathode of the invention advantageously can be combined with the FE cathode gating technique of the invention. It should be understood, however, that both the planar focusing cathode of the invention and the FE cathode gating technique of the invention represent different basic technologies and techniques and should be considered independently on their own merits.

FIG. 10 illustrates an exemplary application of the gun of the invention, for example, as illustrated in FIGS. 1 and 8 in accordance with the present invention. The initial goals for this design were based on the needs for electron microscopy. Thus, emphasis was placed on reducing the beam emittance (i.e. improving transverse quality) and energy spread, while generating modest beam currents. For these simulations, the chosen bunch charge was 0.385 pC, or an average beam current of 0.5 mA if an electron bunch is produced every RF period. The electron charge distribution was generated initially according to the profile shown above, and later approximated by a Gaussian distribution.

In FIG. 10 there is shown an exemplary simulated beamline layout generally designated by the reference character 1000 in accordance with the present invention. An energy filter 1002 introduces a correlation between the beam energy and position, allowing a narrow slice to be transmitted from the core of the beam. This results in both a reduced energy spread and an improved transverse quality, because the core of the beam generally is the portion where the transverse quality is highest. PARMELA was used to simulate the entire beamline. A Gaussian longitudinal distribution was used as a surrogate for the actual FE cathode emission profile, for ease of scaling to larger particle counts. The electron gun 100 coupled to the energy filter 1002 is a multifrequency FE cathode gun as described above. A cathode 0.1 mm in diameter was assumed, generating an initial beam current of 0.5 mA on average. The applied fields were as those above, with a peak field on the cathode of about 25 MV/m. The energy filter was set to transmit about 20% of the beam current, or 0.1 mA. Finally, a first-harmonic linearizer 1004 reduces the beam energy spread by 2 orders of magnitude and a third-harmonic linearizer 1006 reduced the beam energy spread by another order of magnitude.

At the end of this simulated beamline, the beam current is about 90 µA. The average beam energy is 1.786 MV. The root mean square (RMS) fractional energy spread is $1.7 \cdot 10^{-5}$, or about 30 volts in absolute terms. The horizontal and vertical normalized emittances are $1.2 \cdot 10^{-3}$ and $1.0 \cdot 10^{-3}$ µm, respectively. The difference arises because the energy filter 1002 bends the beam in the horizontal plane. This should be sufficient to generate a beam spot about 1 nm in radius, given good electron-beam optics. The total electron beam power is about 180 W. The beam power from the gun is closer to 900 W; the scrapers in the energy filter absorb the difference. Therefore, the power density on at the spot could in principle be approximately 51 GW per square mm. Further reducing the transmission of the filter will result in additional improvements to beam quality, at the expense of current.

It should be understood that the present invention is not limited to the illustrated application of FIG. 10. For example, if the energy filter 1002 is removed from the beamline, thereby passing all of the beam current, the first-harmonic linearizer 1004 and the third-harmonic linearizer 1006 can still be used to reduce the beam energy spread. In this case, the beam energy is around 1.4 MV and the final energy spread is $1.7 \cdot 10^{-4}$ rms (or about 300 volts). The beam energy is lower than above, and the energy spread is larger, because the energy filter 1002 is not removing the "wings" of the incoming electron beam. Thus, a different minima for the energy spread is found. The transverse quality is also worse, at about $4 \cdot 10^{-3}$ µm. On the other hand, the entire beam current of 0.5 mA is transmitted, for a final beam power of about 700 W.

As a comparison, a typical electron beam welder might have a beam power of 15 kW, with a voltage of 60 kV. Thus, although the beam power is higher, the e-beam welder's beam energy is lower by a factor of 20. The beam from the multifrequency gun 100 should therefore penetrate more deeply into the material, and should almost certainly be able to provide higher-precision, smaller-area welds.

It should be understood that the beam power, 700 W, can easily be provided for by relatively compact, CW RF power sources. This would result in an e-beam welder that is smaller and more compact, due to the elimination of need for high-voltage DC power supplies.

Also if the cathode radius were to be doubled, to 0.2 mm, and the beam current increased by an order of magnitude, to 5 mA, the final energy spread remains approximately the same at $10.8 \cdot 10^{-4}$, and the emittance increases to $2.6 \cdot 10^{-2}$ µm, roughly in proportion to the electron beam current. The beam power increases to 7 kW.

The penetration of an electron beam into matter scales (at low energies) approximately as:

$$\delta z \approx 0.1 \cdot E^{1.5}/\rho \qquad (2)$$

where $\delta z$ is the penetration depth in µm, E is the beam energy in kV, and $\rho$ is the material density in g/cm$^3$. This is an empirical formula, but is in reasonable agreement with theoretical calculations. For instance, a 15 kV electron beam should penetrate about 2.3 µm into a silicate material with a density of 2.5 g/cm$^3$.

Given a notional 100 kV beam energy for an electron microscope, the beam from the FE cathode gun, configured to run with the energy filter and a final beam energy of 1.7 MeV, could be expected to penetrate approximately 70 times as deeply into a sample, all other things being equal.

For a typical electron beam welder operating at 60 kV, the expected penetration depth into iron or copper would be around 5.5 µm. (Actual welds can go much deeper due to heat diffusion etc.) The beam from the FE cathode gun without the energy filter, with a final beam energy of 1.4 MeV, should penetrate 0.6 mm, more than 100 times as deep, and therefore depositing more of the electron beam energy into the volume of the metal as opposed to on the surface.

In brief, the disclosed method for gating the emission from a field-emission cathode makes the FE cathode a viable choice for high-brightness RF electron gun design. The beam quality is improved via standard post-gun manipulations. Performance figures were calculated for an electron microscope; the results also indicate that a compact, precision electron-beam welder can be constructed using an almost identical beamline.

Also when superconducting cavities are used for the gun and linearizer cavities, there is effectively no power lost in the cavity walls and the RF power system can consist of relatively low-power, compact oscillator sources. This would maintain a relatively compact footprint for an electron microscope device, and should potentially reduce the footprint for an electron-beam welder.

Other applications of interest include the use of the gun and linearizer to provide beam for a compact free-electron laser operating in the THz region.

FIG. 11 provides a detail view of a novel cathode 102 that provides a focused electron beam in accordance with the present invention. Cathode 102 is a planar focusing cathode. The planar focusing cathode includes a selected dielectric material 120, such as a ceramic material, to provide an electron beam emission surface 130. A first metal surface 122 and conducting wall 110 respectively are provided both behind and in front of the dielectric material 120 to shape the electric fields that accelerate and guide the beam from the cathode surface 130. The dielectric material 120 can be penetrated by electric fields, allowing the planar focusing cathode 102 to provide focusing for the electron beam starting at the substantially flat surface 130 of the cathode dielectric material 120. The first metal surface or shorting plunger 122 behind the dielectric material 120 is slidingly positioned in a cavity or vacuum 124 relative to the dielectric material 120. The distance between the shorting plunger 122 and the dielectric material 120 determines the effective focusing force applied to an electrode beam, for example, as illustrated in FIG. 13

FIG. 12 illustrates exemplary electric field contours of the planar focusing cathode 1100 of FIG. 11 in accordance with the present invention.

FIG. 13 illustrates an exemplary normalized radial electric field at the cathode surface of the planar focusing cathode of FIG. 11 in accordance with the present invention. In FIG. 13 a radial electric field at the cathode surface is shown that is normalized to the longitudinal field, as a function of radius, for three different positions of the plunger 122.

Figure 14:
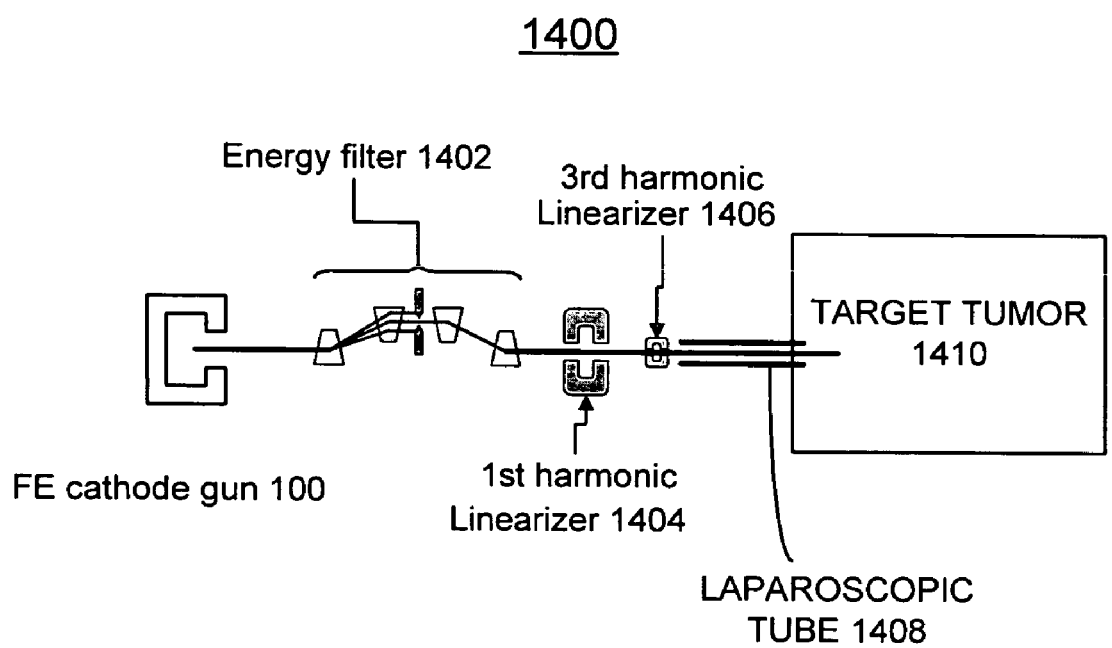
FIG. 14 is a schematic diagram illustrating an exemplary tumor therapy apparatus including the RF electron gun of FIG. 1 for implementing laparoscopic tumor therapy methods in accordance with the present invention.

Having reference now to FIG. 14, there is shown exemplary tumor therapy apparatus generally designated by the reference character 1400 including the RF electron gun 100 for implementing laparoscopic tumor therapy methods in accordance with the present invention.

In accordance with features of the invention, the RF electron gun 100 with Field Emission Cathode Gating and Planar Focusing Cathodes of the preferred embodiment is used as the electron source 100 for implementing tumor therapy methods in accordance with the present invention. The high power, long focus electron source 100 generates an e-beam. Tumor therapy apparatus 1400 includes an energy filter 1402 introducing a correlation between the beam energy and position, a first-harmonic linearizer 1404 that reduces the beam energy spread by 2 orders of magnitude, and a third-harmonic linearizer 1406 reducing the beam energy spread by another order of magnitude. The e-beam is focused and transported through the energy filter 1402 and linearizers 1404 and 1406 into a laparoscope tube 1408 that is located proximate a target tumor 1410 for electron irradiation therapy.

The laparoscopic tube 1408 is important to the invention. The tube 1408 must be aligned to the long-focus electron source 100 to transport the e-beam efficiently to the target tumor 1410. The laparoscopic tube 1408 could be as simple as a small hollow metal tube filled with air. However some of the e-beam would scatter off of air molecules and irradiate surrounding tissue. An improved tube 1408 would be either filled with He gas, or even better, evacuated to reduce gas scatter and reduce unwanted irradiation.

In accordance with features of the invention, to perform the tumor therapy, a small incision is made proximate a target tumor 1404 inside a patient's body and the laparoscopic tube 1408 then is inserted and positioned to the edge of the tumor. The long-focus electron source 100 is positioned to align with the laparoscopic transport tube 1408. The tumor is then electron irradiated. The laparoscopic tube 1408 is a hard-walled laparoscopic tube that shields other body parts from irradiation. Electrons attenuate in very short distances in solids, while x-rays, neutrons, and protons have long attenuation paths. By tuning energy of the e-beam output of the RF electron gun 100, the e-beam substantially is absorbed in the target tumor 1410 substantially without affecting surrounding body tissue. As a result the amount of unnecessary tissue radiation is minimized.

In accordance with features of the invention, an articulated electron beam transport system is used with the high power, long focus electron source 100 for tumor therapy that allows the transport of an electron beam to a target cancer site or target tumor 1410 with minimally invasive surgery. The articulated electron beam transport system is illustrated and described with respect to FIGS. 15-22 includes one of a focusing/defocusing (FODO) lattice with each element articulated; a FODO with cell-by-cell articulation; or a solenoid lens transport. The articulated laparoscopic tube 1408 is able to steer the e-beam through an arc with a radius of curvature of 0.75 m. The curved laparoscopic tube 1408 transports the e-beam to the target tumor 1410 when it would be difficult to use a straight, line-of-sight laparoscopic tube.

Figure 15:
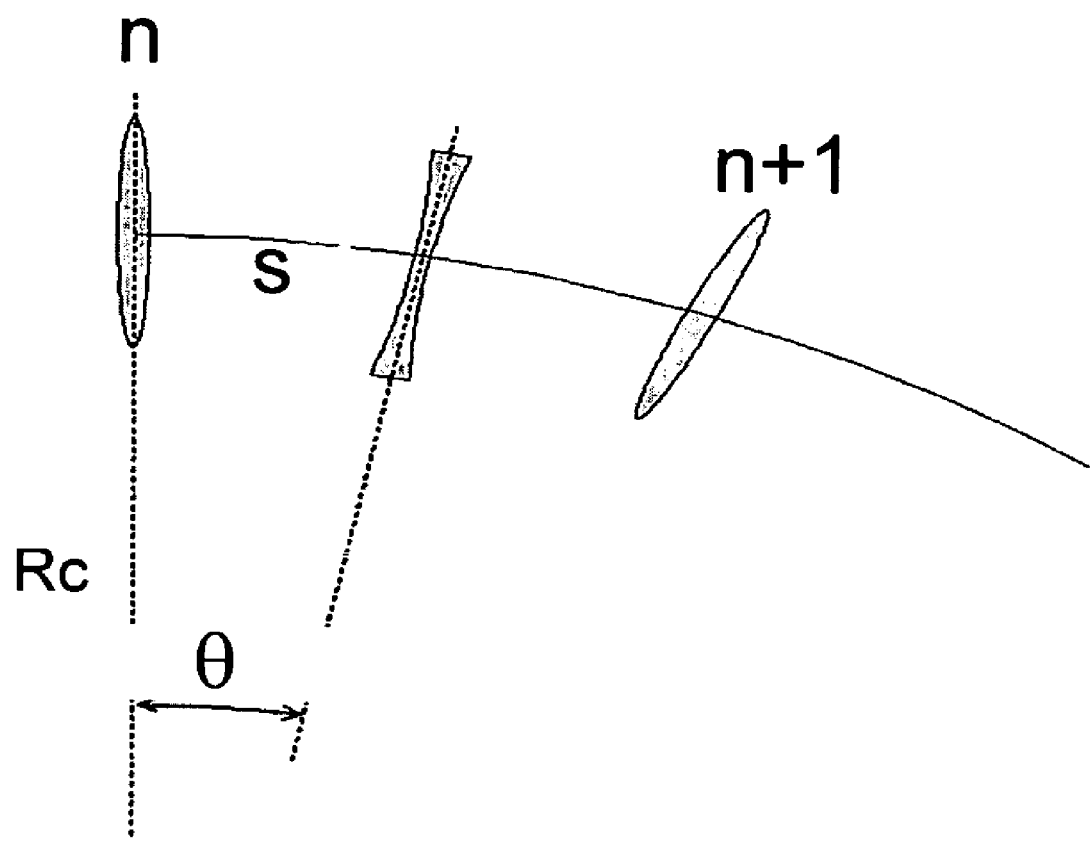
FIG. 15 illustrates a focusing/defocusing (FODO) lattice electron-beam transport optical system with each element of the FODO lattice articulated in accordance with the present invention.

FIG. 15 illustrates a focusing/defocusing (FODO) lattice generally designated by the reference character 1500 for implementing an electron-beam transport optical system in accordance with the present invention. FODO lattice 1500 includes multiple cells with two cells shown and labeled n and n+1. Generally all elements in a FODO lattice are collinear. In FIG. 15, a fully articulated FODO lattice geometry is illustrated where n is the cell number, s the spacing between elements in the cell, 2 s is the cell length, and θ is the bend angle between each element in the FODO cell. For a flexible endoscope application, the FODO lattice 1500 is arranged with each element n, n+1 being articulated, as indicated in FIG. 15.

In a first study of FODO lattice 1500, a thin-lens approximation (i.e. zero-length elements) is used. Under these conditions, the transport of an electron through a single FODO can be written as:

$$\begin{pmatrix} x_{n+1} \\ x'_{n+1} \end{pmatrix} = \begin{pmatrix} 1 & 0 \\ -\frac{1}{f} & 1 \end{pmatrix} \cdot \begin{pmatrix} 1 & L \\ 0 & 1 \end{pmatrix} \cdot \begin{pmatrix} 1 & 0 \\ \frac{2}{f} & 1 \end{pmatrix} \cdot \begin{pmatrix} 1 & L \\ 0 & 1 \end{pmatrix} \cdot \begin{pmatrix} 1 & 0 \\ -\frac{1}{f} & 1 \end{pmatrix} \cdot \begin{pmatrix} x_n \\ x'_n \end{pmatrix} \quad (1)$$

where ($x_n$, $x'_n$) represent the particle position and trajectory angle at the entrance to cell n, f is the focal length of the lenses, and L is the spacing between the lenses. Adding a bend angle 2θ to the cell as a whole, unfortunately, breaks the matrix formalism as some additional terms have to be added to Equation (1) in a linear, as opposed to proportional fashion. The result of adding the bending terms is (in an unreduced form):

$$T_\theta(x, x', s, f, \theta) := \quad (2)$$

$$\begin{pmatrix} 1 & 0 \\ -\frac{1}{f} & 1 \end{pmatrix} \cdot \begin{bmatrix} \left[\left(1 + 2 \cdot \frac{s}{f}\right) \cdot \left[\frac{(x \cdot f - x \cdot s + s \cdot x' \cdot f)}{(f \cdot \cos(\theta))} + s \cdot \theta\right] + s \cdot \left[\frac{(-x + x' \cdot f)}{f} + \theta\right]\right] \cdot \frac{1}{\cos(\theta)} + s \cdot \theta \\ \frac{2}{f} \cdot \left[\frac{(x \cdot f - x \cdot s + s \cdot x' \cdot f)}{(f \cdot \cos(\theta))} + s \cdot \theta\right] + \frac{(-x + x' \cdot f)}{f} + 2\theta \end{bmatrix}$$

where $T_\theta$ is a transfer function providing a 2×1 output coordinate matrix through a single cell, x and x' are the input particle coordinates, s is the spacing between the focusing elements, f is the focal length of the lens elements, and θ is the bend angle between the elements. (The final matrix multiplication is not performed because the resulting 2×1 matrix would extend for several lines without adding any physical insight.)

In this configuration, transport is not necessarily stable for an infinite number of cells. The transport is stable, however, for a reasonable number of cells, say 10, which should suffice to allow transport through a reasonable-length line.

Figure 16:
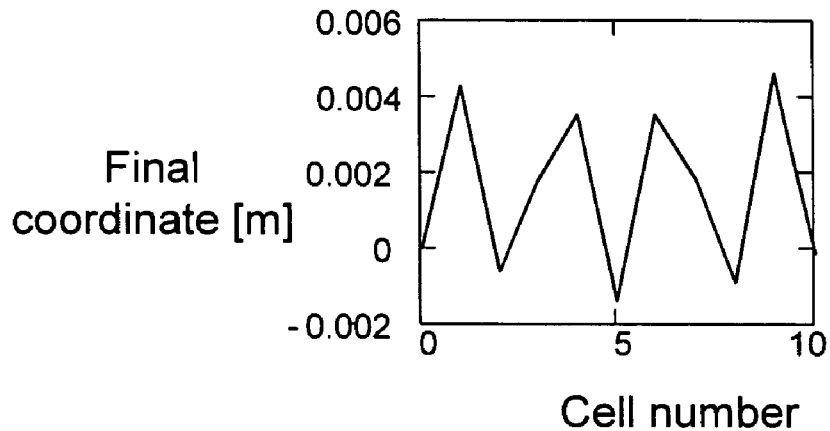
FIG. 16 illustrates final coordinate $x_n$ for transport through 10 cells of the FODO lattice of FIG. 15 in accordance with the present invention.

Referring to FIG. 16, there is shown final coordinate $x_n$ for transport through 10 cells of the FODO lattice of FIG. 15 in accordance with the present invention. Note the very gradual increase of output position over distance. In this case, the total transport line corresponds to a physical extent of 10 cm, with a full-cell bend angle of 20 degrees; the entire transport line is therefore bent through 200 degrees. In FIG. 16, there is shown an ending beam position for a bent transport line, with a reference particle injected at x=−1 mm. The transport line parameters are: s=5 mm; θ=10 deg; f=5.5 mm; $x_0$=−1 mm; $x'_0$=0.

For a thick lens treatment, the thin-lens approximation matrix elements used in Equation (1) can be replaced, in a straightforward fashion, with the full matrix representation. The substitution used is:

$$\begin{pmatrix} 1 & 0 \\ -\frac{1}{f} & 1 \end{pmatrix} \rightarrow \begin{pmatrix} \cos\left(\frac{L}{2}\sqrt{k_o}\right) & \frac{1}{\sqrt{k_o}}\sin\left(\frac{L}{2}\sqrt{k_o}\right) \\ -\sqrt{k_o}\sin\left(\frac{L}{2}\sqrt{k_o}\right) & \cos\left(\frac{L}{2}\sqrt{k_o}\right) \end{pmatrix} \quad (3a)$$

$$\begin{pmatrix} 1 & 0 \\ \frac{2}{f} & 1 \end{pmatrix} \rightarrow \begin{pmatrix} \cosh\left(\frac{L}{2}\sqrt{k_o}\right) & \frac{1}{\sqrt{k_o}}\sinh\left(\frac{L}{2}\sqrt{k_o}\right) \\ \sqrt{k_o}\sinh\left(\frac{L}{2}\sqrt{k_o}\right) & \cosh\left(\frac{L}{2}\sqrt{k_o}\right) \end{pmatrix} \quad (3b)$$

where L is the full length of the quadrupole lenses, and $k_0$ is the normalized focusing strength.

Substituting this into the equations used above results in a very long expression, which would serve no purpose reproduced here. The results are somewhat more sensitive, as expected, to bend angle than the results shown above, but not by much.

Figure 17:
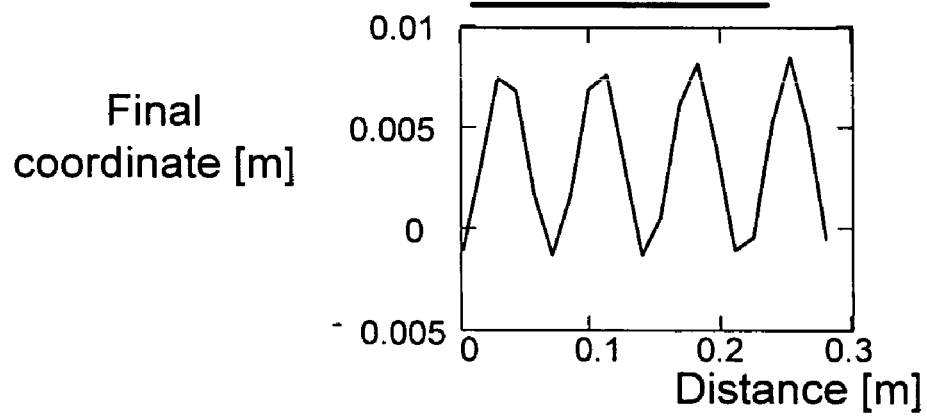
FIG. 17 illustrates final coordinate $x_n$ and results similar to FIG. 16 for a thick lens transport channel in accordance with the present invention.

Referring also to FIG. 17, results of a 14-degree bend per cell are shown. FIG. 17 illustrates final coordinate $x_n$ and results similar to FIG. 16 for a thick lens transport channel in accordance with the present invention. FIG. 17 illustrates the output coordinates from the thick-lens transport channel with the following parameters: s=5 mm; L=2 mm, $k_o$=9·10$^4$ (for similar net focusing terms); θ=7 deg; $x_0$=−1 mm; $x'_0$=0.

Figure 18:
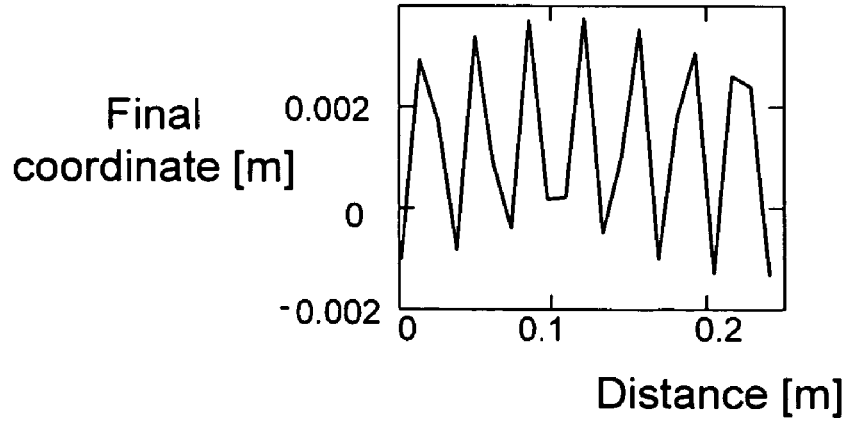
FIG. 18 illustrates final coordinate $x_n$ and results similar to FIG. 17 for very thick lenses, separated by small drifts in accordance with the present invention.

Referring also to FIG. 18 final coordinate $x_n$ and results are shown similar to FIG. 17 for very thick lenses, separated by small drifts in accordance with the present invention. FIG. 18 shows results of a calculation using the opposite of the thin-lens approximation: very thick lenses, separated by small drifts. Note that the total amplitude has been reduced by approximately a factor of two. FIG. 18 illustrates the output coordinates from a thick-lens transport channel, with the following parameters: s=1 mm; L=5 mm; all other parameters are as indicated in FIG. 17.

Another interesting scenario is found by noting the periodicity found in these solutions. This suggests that the transport line might be "pre-curved," such that the largest amplitude excursion takes place outside the body; the transport line diameter could then be tapered down as a function of distance to the final target location.

For a FODO lattice 1500 with inter-cell articulation, a second study uses a FODO cell similar to the one described above. In this case, however, the articulation point is taken to be at the junction of two cells, not between each element within a cell. This has certain advantages from both a construction and an analytical standpoint. From the construction standpoint, fewer moving parts are needed and a more standard cell would allow for a more readily modifiable (e.g. extensible) beamline transport system. From the analytical standpoint, each FODO cell is linear; the articulation at the end of each cell appears as a coordinate system translation and shift. This makes the overall analysis easier.

For this study, the complete 1$^{st}$-order transverse uncoupled quadrupole transport matrix is used. For the horizontally focusing/vertically defocusing quadrupole, the matrix is:

$$Q_f(k_o, L) := \begin{pmatrix} \cos(\sqrt{k_o} \cdot L) & \frac{1}{\sqrt{k_o}} \cdot \sin(\sqrt{k_o} \cdot L) & 0 & 0 \\ -\sqrt{k_o} \cdot \sin(\sqrt{k_o} \cdot L) & \cos(\sqrt{k_o} \cdot L) & 0 & 0 \\ 0 & 0 & \cosh(\sqrt{k_o} \cdot L) & \frac{1}{\sqrt{k_o}} \sinh(\sqrt{k_o} \cdot L) \\ 0 & 0 & \sqrt{k_o} \cdot \sinh(\sqrt{k_o} \cdot L) & \cosh(\sqrt{k_o} \cdot L) \end{pmatrix}; \quad (4)$$

For the horizontally defocusing/vertically focusing quadrupole the matrix is:

$$Q_d(k_o, L) := \begin{pmatrix} \cosh(\sqrt{k_o} \cdot L) & \frac{1}{\sqrt{k_o}} \cdot \sinh(\sqrt{k_o} \cdot L) & 0 & 0 \\ \sqrt{k_o} \cdot \sinh(\sqrt{k_o} \cdot L) & \cosh(\sqrt{k_o} \cdot L) & 0 & 0 \\ 0 & 0 & \cos(\sqrt{k_o} \cdot L) & \frac{1}{\sqrt{k_o}} \sin(\sqrt{k_o} \cdot L) \\ 0 & 0 & -\sqrt{k_o} \cdot \sin(\sqrt{k_o} \cdot L) & \cos(\sqrt{k_o} \cdot L) \end{pmatrix}; \quad (5)$$

and for the drift space between the cells, the matrix is:

$$D(L) := \begin{pmatrix} 1 & L & 0 & 0 \\ 0 & 1 & 0 & 0 \\ 0 & 0 & 1 & L \\ 0 & 0 & 0 & 1 \end{pmatrix}. \quad (6)$$

The definitions of $k_o$ and L are the same as used above.

To avoid articulating the beamline in the middle of a quadrupole, the FODO cell is defined slightly differently here to consist of a whole focusing quadrupole, drift, defocusing quadrupole, and drift, as opposed to the above section, which assumed half-length focusing quadrupoles on each end of the cell. The net results are matrices that look somewhat different, but which have the same net behavior as far as the beam transport is concerned.

Using Eqns. (4)-(6) we can define a function, $T_n$, which transfers a particle from the start of the FODO cell to the end, as:

$$T_n(x, x', y, y', s, L, k_o, \theta_x, \theta_y) := \quad (7)$$

$$D(s) \cdot Q_d(k_o, L) \cdot D(s) \cdot Q_f(k_o, L) \cdot \begin{pmatrix} x \\ x' \\ y \\ y' \end{pmatrix}$$

where $k_o$ is the normalized quadrupole strength, L is the length of the quadrupole, s is the length of the drift space between the quadrupoles, (x,x') represent the horizontal starting position and angle, and (y,y') represent the vertical starting position and angle. The angles $\theta_x$ and $\theta_y$ are placeholders for the horizontal and vertical bend angles, respectively, at the end of the cell, left in this definition to allow comparison of straight vs. bent transport lines; they have no impact on $T_n$'s values in the above formulation. $T_n$ is a 4×1 column vector.

The coordinate transform and shift at the end of the cell is performed by a multiplication and addition to $T_n$, $$T_{\theta\theta}(x, x', y, y', s, L, k_o, \theta_x, \theta_y) := \quad (8)$$

$$\begin{pmatrix} s \cdot \theta_x \\ \theta_x \\ s \cdot \theta_y \\ \theta_y \end{pmatrix} + \begin{pmatrix} \frac{1}{\cos(\theta_x)} & 0 & 0 & 0 \\ 0 & 1 & 0 & 0 \\ 0 & 0 & \frac{1}{\cos(\theta_y)} & 0 \\ 0 & 0 & 0 & 1 \end{pmatrix} \cdot T_n(x, x', y, y', s, L, k_o, \theta_x, \theta_y)$$

where $\theta_{x,y}$ are the bend angles as described above. Equation (8) shows explicitly how the bends are treated as a modification to the $T_n$ function in Equation (7).

Equation (8) can, as was done previously, be iterated from step to step to determine the output coordinate of a particle at the end of a given cell. This iterative approach also allows the bend angles to be changed as a function of cell number to better simulate an actual transport path. There are two caveats. First, the equations are uncoupled in that there is no cross talk between x and y. In physical terms, this means that the transport line can bend in either direction, but cannot be twisted. Second, the results do not take into account energy spread. Off-energy particles can be treated by adjusting the value of $k_o$, the magnetic focusing strength, based on the particle energy.

Figure 19:
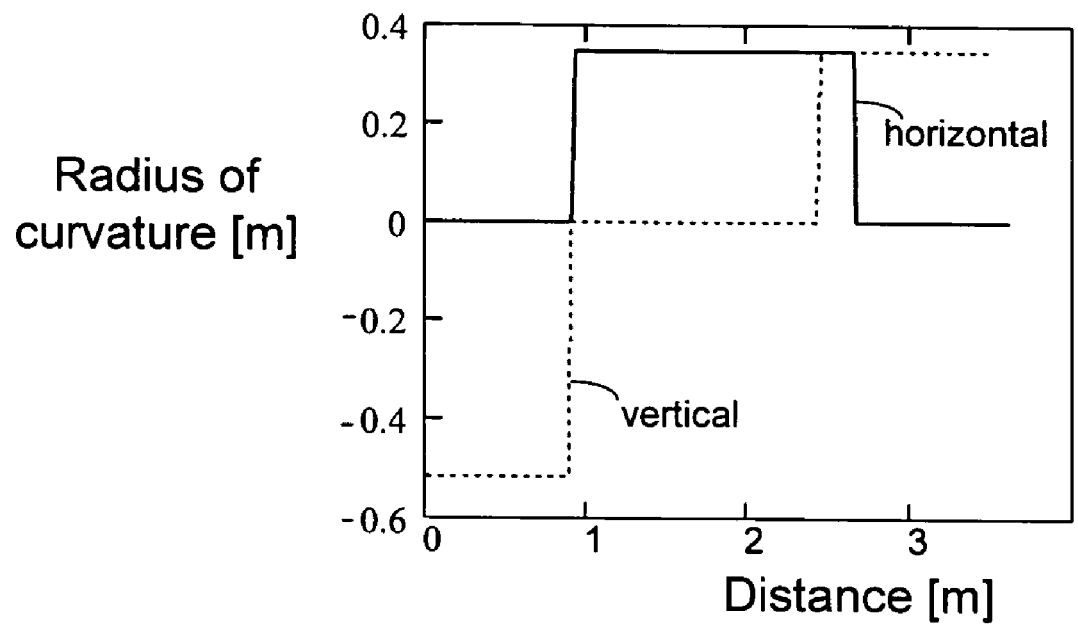
FIG. 19 illustrates bend angles in the form of radii of curvature, indicating the horizontal x and vertical y planes for the transport path in accordance with the present invention.

FIG. 19 illustrates bend angles, in the form of radii of curvature, indicating the horizontal x and vertical y planes for the transport path in accordance with the present invention. In FIG. 19, the radii of curvature are shown as a function of distance down the transport path. Simulation parameters are: s=5 mm; L=4 mm; $k_o=200^2$, $x_0=y_0=x'_0=y'_0=0$. The simulation incorporates 200 FODO cells.

Figure 20:
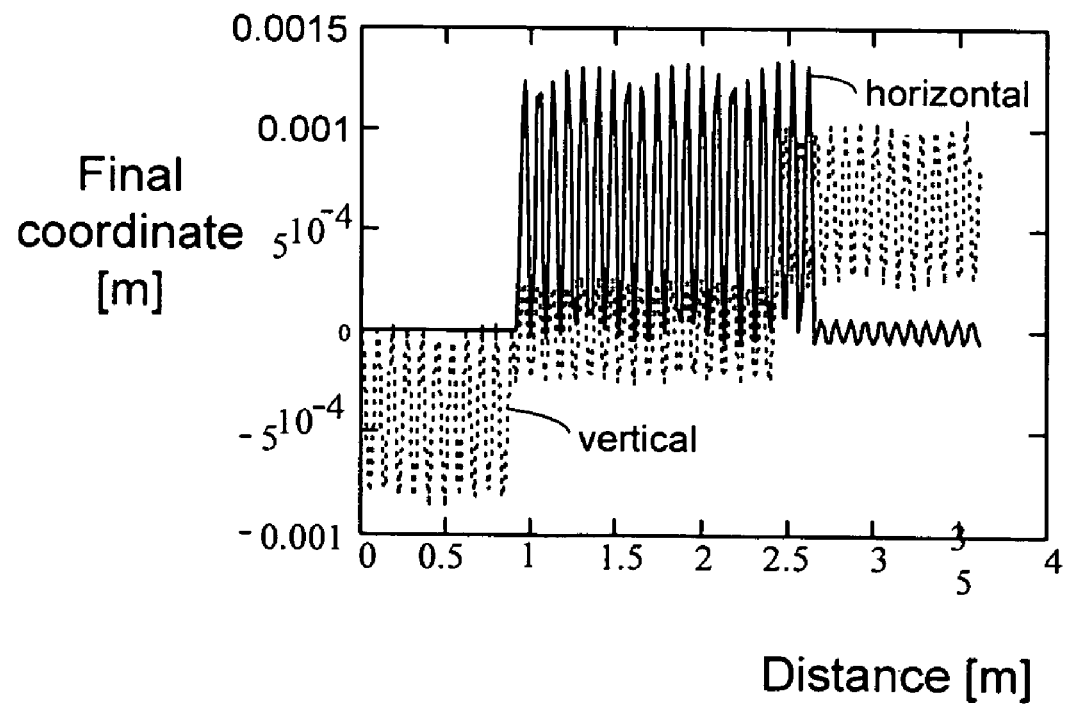
FIG. 20 illustrates beam envelope for the parameters and radii of curvature shown in FIG. 19 in accordance with the present invention.

FIG. 20 illustrates beam envelope for the parameters and radii of curvature shown in FIG. 19 in accordance with the present invention.

A judicious choice of where to place the articulation joints may lead to better performance in one or both planes, however, this is a relatively small effect overall.

Figure 21:
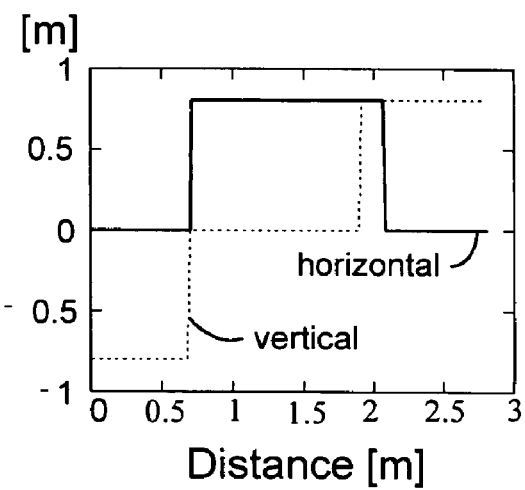
FIGS. 21 and 22 respectively illustrate results of a segmented solenoid-based articulated transport line in accordance with the present invention.
Figure 22:
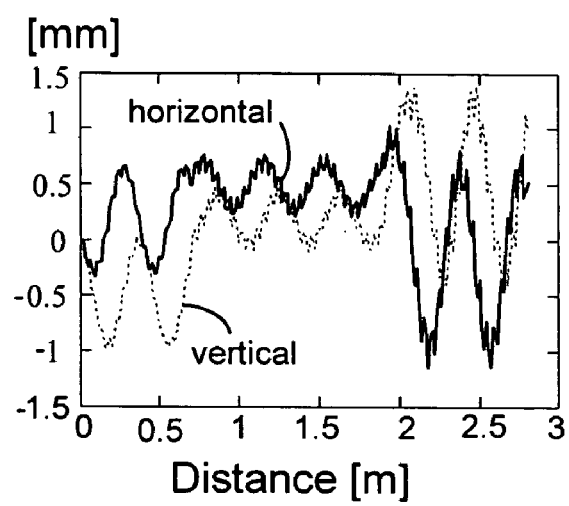

Having reference to FIGS. 21 and 22, results of a solenoidal-lens based transport are illustrated. FIGS. 21 and 22 respectively illustrate results of a segmented solenoid-based articulated transport line in accordance with the present invention. The transfer matrix for solenoids is very complex due to the cross-coupling of the horizontal and vertical planes. However, the same basic formulation as used with the articulated-cell transport line above can be used. Doing so yields results such as those shown in FIGS. 21 and 22. FIG. 21 shows the bend radii of the transport line in the x and y planes and FIG. 22 shows the trajectory of an on-axis-injected particle through the transport channel. Solenoid effective length=9 mm; inter-solenoid gap=5 mm; solenoid field=1 T; $x_0=y_0=x'_0=y'_0=0$. Simple checks show that transport line radii of curvature down to 0.75 m are feasible with the parameters shown in FIGS. 21 and 22.

In brief summary, it should be understood that an articulated electron beam transport line, based on either element-by-element or cell-by-cell articulation, is possible. The required magnet strengths are high, but not unreasonable given current magnet technology. Further, the resulting radii of curvature would appear to be small enough to be useful in various applications.

The cell-by-cell articulation scheme appears to be the more promising for several reasons. First, it is physically simpler, both in terms of initial construction and in terms of later modifications. Second, the underlying mathematical description is more straightforward, allowing for easier analysis of the resulting model.

Finally, the success of the articulated-cell FODO transport line provides an important result: Since the FODO cell is net-focusing in both planes; it is possible to design a comparable transport system with any net-focusing optical elements. This includes geometries that generate radially symmetric fields such as ring magnets and current coils. In the limit of high coil count and small coil spacing, a current-coil configuration is identical to a solenoid. The mathematical treatment of a solenoid system is not as straightforward as for a quadrupole, due to the coordinate-system rotation imposed by the solenoidal field. It would appear, however, that a solenoidal-based transport system, as a net-focusing system, should also function properly.

While the present invention has been described with respect to the RF cathode gun 100 of the preferred embodiment that is needed to treat deep body cavity tumors, it should be understood that the laparoscopic tube can be used with existing high power electron sources to treat tumors that are near to the body surface or near surface tumors, for example, breast cancer tumors.

While the present invention has been described with reference to the details of the embodiments of the invention shown in the drawing, these details are not intended to limit the scope of the invention as claimed in the appended claims.

What is claimed is:

1. A laparoscopic tumor therapy method comprising the steps of:
providing a high power, long focus electron source for generating an e-beam;
tuning beam energy and focusing the e-beam:
transporting the focused e-beam through a laparoscopic tube proximate to a target tumor for electron irradiation therapy, said laparoscopic tube shielding other body parts from irradiation with the focused e-beam substantially absorbed in the target tumor.

2. A laparoscopic tumor therapy method as recited in claim 1 wherein the step of providing a high power, long focus electron source for generating an e-beam includes the steps of utilizing field-emitter cathodes for radio frequency (RF) electron guns and altering the emission time of a field-emitter (FE) cathode with respect to the RF period in an RF electron gun including:
adjusting both phase and strength of a predefined harmonic field relative to a fundamental field to cause a field emission cathode to emit electrons at predefined times for generation of high-brightness electron beams, whereby emission time is gated responsive to the combined harmonic and fundamental fields and a response of the FE cathode to the combined fields.

3. A laparoscopic tumor therapy method as recited in claim 1 wherein the step of tuning beam energy and focusing the e-beam includes the steps of transporting the e-beam through an energy filter and at least one harmonic linearizer into said laparoscopic tube, and wherein the step of transporting the focused e-beam through a laparoscopic tube includes the steps of providing a hard-walled laparoscopic tube; and aligning said high power, long focus electron source with said hard-walled laparoscopic tube.

4. A laparoscopic tumor therapy method as recited in claim 3 includes the steps of providing an incision proximate the target tumor; and inserting and positioning said hard-walled laparoscopic tube through said incision and proximate the target tumor.

5. A laparoscopic tumor therapy method as recited in claim 1 includes the step of providing an articulated electron beam transport system with the high power, long focus electron source.

6. A laparoscopic tumor therapy method as recited in claim 1 wherein said articulated electron beam transport system includes a selected one of a focusing/defocusing (FODO) lattice with each element articulated; a FODO lattice with cell-by-cell articulation; and a solenoid lens transport.

7. Laparoscopic tumor therapy apparatus comprising:
a high power, long focus electron source for generating an e-beam;

an energy filter and at least one harmonic linearizer, coupled to said high power, long focus electron source, tuning beam energy and focusing the e-beam; and an articulated electron beam transport system for receiving the focused e-beam and transporting the focused e-beam through a laparoscopic tube proximate to a target tumor for electron irradiation therapy, said laparoscopic tube shielding other body parts from irradiation with the focused e-beam substantially absorbed in the target tumor.

8. Laparoscopic tumor therapy apparatus as recited in claim 7 wherein said high power, long focus electron source for generating an e-beam includes an RF electron gun having a planar focusing cathode for providing a focused electron beam having a selected dielectric material for providing an electron beam emission surface; said electron beam emission surface including a substantially flat surface; a first metal surface behind said dielectric material; a second metal surface radially surrounding said dielectric material; said first metal surface and said second metal surface for shaping electric fields that accelerate and guide an electron beam from the electron beam emission surface; and said dielectric material being penetrated by electric fields and allowing the planar focusing cathode to provide focusing of said electron beam starting at said substantially flat surface of the cathode dielectric material.

9. Laparoscopic tumor therapy apparatus as recited in claim 8 wherein selected dielectric material includes a ceramic material; and said selected dielectric material functions as a cathode of a high brightness RF electron gun and provides focusing of said electron beam.

10. Laparoscopic tumor therapy apparatus as recited in claim 7 wherein said laparoscopic tube includes a hard-walled laparoscopic tube; and e-beam output of said high power, long focus electron source is aligned with said hard-walled laparoscopic tube.

11. Laparoscopic tumor therapy apparatus as recited in claim 7 wherein said articulated electron beam transport system includes a focusing/defocusing (FODO) lattice with each element articulated.

12. Laparoscopic tumor therapy apparatus as recited in claim 7 wherein said articulated electron beam transport system includes a focusing/defocusing (FODO) lattice with cell-by-cell articulation.

13. Laparoscopic tumor therapy apparatus as recited in claim 7 wherein said articulated electron beam transport system includes a solenoid lens transport.

* * * * *